(12) United States Patent
Nowlin et al.

(10) Patent No.: US 7,778,733 B2
(45) Date of Patent: Aug. 17, 2010

(54) GRIP STRENGTH WITH TACTILE FEEDBACK FOR ROBOTIC SURGERY

(75) Inventors: William C. Nowlin, Los Altos, CA (US); Gary S. Guthart, Foster City, CA (US); Robert G. Younge, Portola Valley, CA (US); Thomas G. Cooper, Menlo Park, CA (US); Craig Gerbi, San Carlos, CA (US); Stephen J. Blumenkranz, Redwood City, CA (US); Dean F. Hoornaert, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 195 days.

(21) Appl. No.: 12/016,556

(22) Filed: Jan. 18, 2008

(65) Prior Publication Data

US 2008/0154246 A1 Jun. 26, 2008

Related U.S. Application Data

(60) Continuation of application No. 11/074,372, filed on Mar. 7, 2005, now Pat. No. 7,373,219, which is a continuation of application No. 10/437,771, filed on May 13, 2003, now Pat. No. 6,879,880, which is a division of application No. 09/544,153, filed on Apr. 6, 2000, now Pat. No. 6,594,552.

(60) Provisional application No. 60/128,157, filed on Apr. 7, 1999.

(51) Int. Cl.
*G05B 15/00* (2006.01)

(52) U.S. Cl. ............ 700/260; 700/245; 700/250; 700/251; 700/254; 700/257; 600/101; 600/102; 600/103; 600/104; 600/118; 606/1; 606/130; 901/1; 901/2; 901/8; 901/9; 901/30

(58) Field of Classification Search .......... 700/245, 700/259, 254, 247, 248, 249, 260; 318/568.11, 318/568.13, 568.16, 573, 574; 901/1, 2, 901/9, 30; 600/101, 102, 103, 104, 118; 606/1, 130
See application file for complete search history.

(56) References Cited

U.S. PATENT DOCUMENTS 4,510,574 A 4/1985 Guittet et al.

(Continued)

FOREIGN PATENT DOCUMENTS

DE 4213426 10/1992

(Continued)

OTHER PUBLICATIONS

Alexander, Arthur D. III, "Impacts of Telemation on Modern Society", Symposium on Theory and Practice of Robots and Manipulators, Centre for Mechanical Sciences 1st CISM IFToMM Symposium, Sep. 5-8, 1974, pp. 121-136, vol. 2, Springer-Verlag.

(Continued)

*Primary Examiner*—Khoi Tran
*Assistant Examiner*—McDieunel Marc

(57) ABSTRACT

Surgical robots and other telepresence systems have enhanced grip actuation for manipulating tissues and objects with small sizes. A master/slave system is used in which an error signal or gain is artificially altered when grip members are near a closed configuration.

8 Claims, 18 Drawing Sheets

U.S. PATENT DOCUMENTS

| | | | |
|---|---|---|---|
| 4,553,746 A * | 11/1985 | Lee | 482/49 |
| 4,696,501 A | 9/1987 | Webb | |
| 4,819,978 A | 4/1989 | Scheinman et al. | |
| 5,184,601 A | 2/1993 | Putman | |
| 5,250,056 A | 10/1993 | Hasson | |
| 5,339,799 A | 8/1994 | Kami et al. | |
| 5,354,162 A | 10/1994 | Burdea et al. | |
| 5,503,320 A | 4/1996 | Webster et al. | |
| 5,572,684 A | 11/1996 | Canik et al. | |
| 5,637,108 A * | 6/1997 | Vidal et al. | 606/1 |
| 5,696,837 A | 12/1997 | Green | |
| 5,697,939 A | 12/1997 | Kubota et al. | |
| 5,762,458 A | 6/1998 | Wang et al. | |
| 5,784,542 A | 7/1998 | Ohm et al. | |
| 5,792,135 A | 8/1998 | Madhani et al. | |
| 5,792,178 A | 8/1998 | Welch et al. | |
| 5,800,423 A | 9/1998 | Jensen | |
| 5,807,377 A | 9/1998 | Madhani et al. | |
| 5,808,665 A | 9/1998 | Green | |
| 5,841,950 A | 11/1998 | Wang et al. | |
| 5,855,553 A | 1/1999 | Tajima et al. | |
| 5,859,934 A | 1/1999 | Green | |
| 5,876,325 A | 3/1999 | Mizuno et al. | |
| 5,931,832 A | 8/1999 | Jensen | |
| 6,024,695 A | 2/2000 | Taylor et al. | |
| 6,113,395 A | 9/2000 | Hon | |
| 6,165,184 A | 12/2000 | Verdura et al. | |
| 6,219,589 B1 | 4/2001 | Faraz et al. | |
| 6,223,100 B1 | 4/2001 | Green | |
| 6,228,097 B1 | 5/2001 | Levinson et al. | |
| 6,231,526 B1 | 5/2001 | Taylor et al. | |
| 6,244,809 B1 | 6/2001 | Wang et al. | |
| 6,259,806 B1 | 7/2001 | Green | |
| 6,280,458 B1 | 8/2001 | Boche et al. | |
| 6,312,435 B1 | 11/2001 | Wallace et al. | |
| 6,323,837 B1 | 11/2001 | Rosenberg | |
| 6,325,808 B1 | 12/2001 | Bernard et al. | |
| 6,331,181 B1 | 12/2001 | Tierney et al. | |
| 6,424,885 B1 | 7/2002 | Niemeyer et al. | |
| 6,451,027 B1 | 9/2002 | Cooper et al. | |
| 6,459,926 B1 | 10/2002 | Nowlin et al. | |
| 6,468,265 B1 | 10/2002 | Evans et al. | |
| 6,491,701 B2 | 12/2002 | Tierney et al. | |
| 6,594,552 B1 | 7/2003 | Gerbi et al. | |
| 2001/0018591 A1 | 8/2001 | Brock et al. | |
| 2001/0056283 A1 | 12/2001 | Carter et al. | |
| 2002/0042620 A1 | 4/2002 | Julian et al. | |
| 2002/0045888 A1 | 4/2002 | Ramans et al. | |
| 2002/0045905 A1 | 4/2002 | Gerbi et al. | |
| 2002/0058929 A1 | 5/2002 | Green et al. | |
| 2005/0149003 A1* | 7/2005 | Tierney et al. | 606/1 |
| 2006/0030840 A1* | 2/2006 | Nowlin et al. | 606/1 |
| 2006/0178559 A1* | 8/2006 | Kumar et al. | 600/109 |
| 2006/0241414 A1* | 10/2006 | Nowlin et al. | 600/431 |
| 2007/0012135 A1* | 1/2007 | Tierney et al. | 74/490.01 |
| 2009/0234371 A1* | 9/2009 | Tierney et al. | 606/130 |

FOREIGN PATENT DOCUMENTS

| | | |
|---|---|---|
| WO | 92/16141 | 10/1992 |
| WO | 93/13916 | 7/1993 |
| WO | 95/01757 | 1/1995 |
| WO | 99/50721 | 10/1999 |
| WO | 01/41052 | 6/2001 |

OTHER PUBLICATIONS

Butner, Steven E. et al., "A real-time system for tele-surgery," IEEE 21st International Conference on Distributed Computing Systems, 2001, pp. 236-243.

Cavusoglu, M.C. et al., A Laparoscopic Telesurgical Workstation, IEEE Transactions on Robotics and Automation, Aug. 1999, pp. 728-739, vol. 15—Issue 4.

Howe, Robert D. et al., Robotics for Surgery Annu. Rev. Biomed. Eng, 1999, pp. 211-242, vol. 1.

Lai, Fuji et al., "Evaluating control modes for constrained robotic surgery," IEEE International Conference on Robotics and Automation, San Francisco, Apr. 2000, vol. 1, pp. 603-609, IEEE.

Mack, Michael J., "Minimally invasive and robotic surgery," JAMA, Feb. 2001, pp. 568-572, vol. 285—Issue 5.

Noonan, David, "The Ultimate Remote Control," NBC Newsweek, Jun. 25, 20011999, p. 71, 7 pages total.

Parsell, D.L., "Surgeons in U.S. perform operation ion France via robot," National Geographic News, Downloaded Sep. 16, 2004, Sep. 19, 2001, pp. 1-5.

Rotnes, J.S. et al., Digital trainer developed for robotic assisted cardiac surgery, Studies in health technology and informatics, 2001, vol. 81, pp. 424-430.

Satava, R. M., Emerging technologies for surgery in the 21st century, Arch Surg, 1999, pp. 1197-1202, vol. 134.

Schaaf, Tracy A., "Robotic surgery: The future is now," MX: Business Strategies for Medical Technology Executives, Medical Device Link, Mar./Apr. 2001, pp. 1-13 Internet http://wwvv.devicelink.com/mx/archive/01/03/0103mx024.html.

Schenker, Paul S. et al., "Development of a Telemanipulator for Dexterity Enhanced Microsurgery," 2ndAnnual International Symposium on Medical Robotics and Computer Assisted Surgery, Nov. 4-7, Baltimore, Maryland, 1995, pp. 81-88.

Taylor, Russell H. et al., Taming the Bull: Safety in a Precise Sugical Robot, Fifth International Conference on Advanced Robotics (91 ICAR), Jun. 19-22, 1991, vol. 1, pp. 865-870, IEEE.

Willett, Edward, "Telesurgery," Internet, 2001, pp. 1-3. Internet http://www.edwardwillett.com/Columns/telesurgery.htm.

Goertz et al., "ANL Mark E4A Electric Master-Slave Manipulator," *Proc. of 14th Conf. on Remote Systems Technology*, pp. 115-123 (1966).

Alexander, "Impacts of Telemation on Modern Society," *First CISM-IFToMM Symposium*, 2:122-136, (Sep. 5, 1973).

Bejozy and Salisbury, "Controlling Remote Manipulators Through Kinesthetic Coupling," *Computers in Mechanical Engineering*, pp. 48-60 (Jul. 1983).

Thring, "Robots and Telechirs: Manipulators with Memory; Remote Manipulators; Machine Limbs for the Handicapped," Ellis Horwood Ltd., pp. 9-11, 122-131, 194-195, 236-257, 274-279 (1983).

Sharpe, "Human factors in the user of covariant bilateral manipulators," *Robot Control Theory and Applications*, Warwick and Pugh (Eds.) Peter Peregrinus Ltd. on behalf of the Institutuon of Electrical Engineers, 24:219-236 (Dec. 1988).

Sabatini et al., "Force Feedback-Based Telemicromanipulation for Robot Surgery on Soft Tissues," *IEEE Engineering in Medicine & Biology Society 11th Annual Int'l Conf.*, pp. 890-891 (Jun. 1989).

Bergamasco et al:, "Advanced Interfaces for Teleoperated Biomedical Robots," *IEEE Engineering in Medicine & Biology Society 11th Annual Int'l Conf.*, pp. 912-913 (Jun. 1989).

Tendick and Stark, "Analysis of the Surgeon's Grasp for Telerobotic Surgical Manipulation," *IEEE Engineering in Medicine & Biology, 11th Annual Int'l Conf.*, pp. 914-915 (Jun. 1989).

Kazerooni, "Design and Analysis of the Statically Balanced Direct-Drive Robot Manipulator," *Robotics and Computer-Integrated Manufacturing*, 6:287-293 (Nov. 4, 1989).

Spain, "Stereo Advantage for a Peg-in-Hole Task Using a Force-Feedback Manipulator," *SPIE* 1256:244-254 (1990).

Lorenz et al., "A Direct-Drive, Robot Parts, and Tooling Gripper with High-Performance Force Feedback Control," *IEEE Transactions on Industry Applications*, 27(2):275-281 (Mar./Apr. 1991).

Yokokohji et al., "Bilateral control of master-slave manipulators for ideal kinesthetic coupling," *IEEE*, pp. 849-858 (1992).

"Remote Robot Control with High Force-Feedback Gain," Technical Support Package, NASA Tech Brief vol. 17, No. 8, Item #49 from JPL New Technology Report NPO-18668 (Aug. 1993).

Sukthankar et al. "Towards Force Feedback in Laparoscopic Surgical Tools," *IEEE*, pp. 1041-1042 (1994).

Hill et al., "Telepresence Surgery Demonstration System," *SRI International, IEEE*, pp. 2302-2307 (1994).

Taubes, Gary, "Surgery in Cyberspace," *Discover*, pp. 85-92. (Dec. 1994).

Taylor et al., "A Telerobotic Assistant for Laparoscopic Surgery," *IEEE Engineering in Medicine and Biology*, pp. 279-288 (May/Jun. 1995).

Charles, "Development of a Telemanipulator for Dexterity Enhanced Microsurgery," *2nd Ann. Int'l Symposium on Medical Robotics and Computer Assisted Surgery*, pp. 81-88 (Nov 4, 1995).

Bauer and Wapler, "Virtual reality as interface for interaction and manipulation in endoscopy," *Minimally Invasive Therapy*, 4:319-339 (1995).

Bluethmann et al., "Experiments in dexterous hybrid force and position control of a master/slave electrohydraulic manipulator," *IEEE*, pp. 27-32 (1995).

Fischer et al., "Tactile Feedback for Endoscopic Surgery," *Interactive Technology and the New Paradigm for Healthcare*, Morgan et al. (Eds.) IOS Press and Ohmsha, 19:114-117 (1995).

Jackson et al., "Force Feedback and Medical Simulation," *Interactive Technology and the New Paradigm for Healthcare*, Morgan et al. (Eds.), IOS Press and Ohmsha, 24:147-151 (1995).

Sukthankar et al., "Force Feedback Issues in Minimally Invasive Surgery," *Interactive Technology and the New Paradigm for Healthcare*, Morgan et al. (Eds.), IOS Press and Ohmsha, 56:375-379 (1995).

Bowersox et al., "Vascular applications of telepresence surgery: initial feasibility studies in swine," *J. Vasc. Surg.*, 23:281-287 (1996).

Hannaford et al., Computerized endoscopic surgical grasper, *IEEE*, pp. 1-7 (1998).

Komatsu et al., Control of a space flexible master-slave manipulator based on parallel compliance models, *IEEE*, pp. 1932-1937 (1998).

Rosen et al., "Force controlled and teleoperated endoscope grasper for minimally invaseive surgery," *IEEE Experimental Performance Evaluation*, 1212-1221 (1999).

Vertut, Jean and Philippe Coiffet, *Teleoperation and Robotics: Evolution and Development*, English translation Prentice-Hall, Inc., Inglewood Cliffs, NJ, USA, 1986.

\* cited by examiner

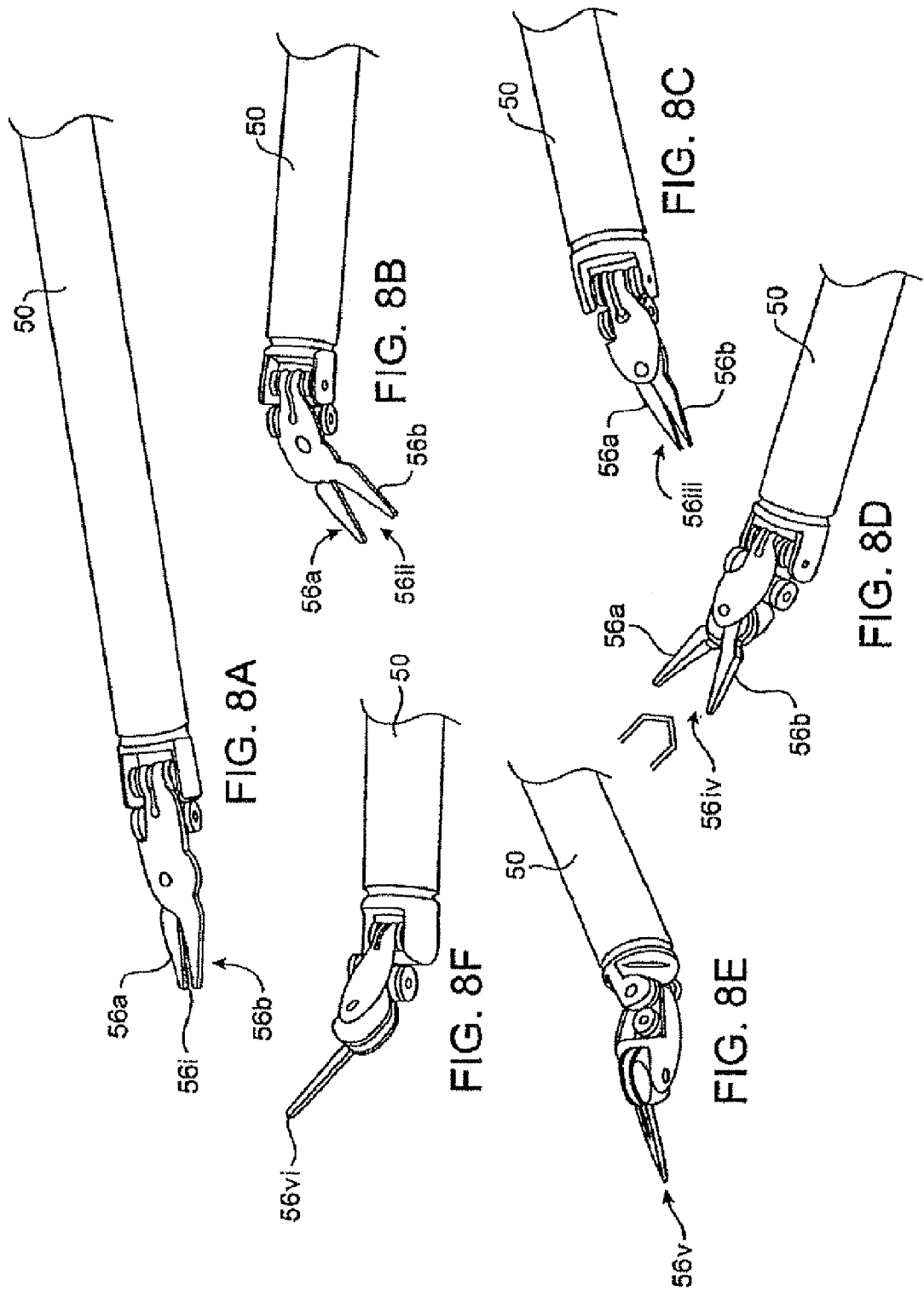

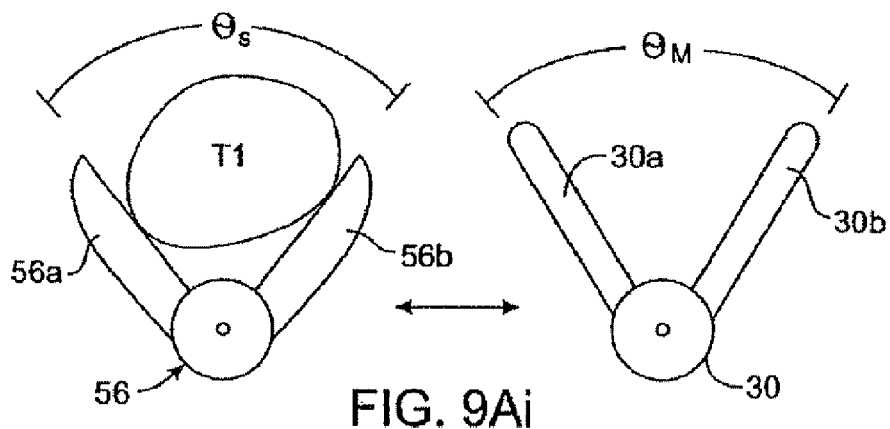
FIG. 9Ai
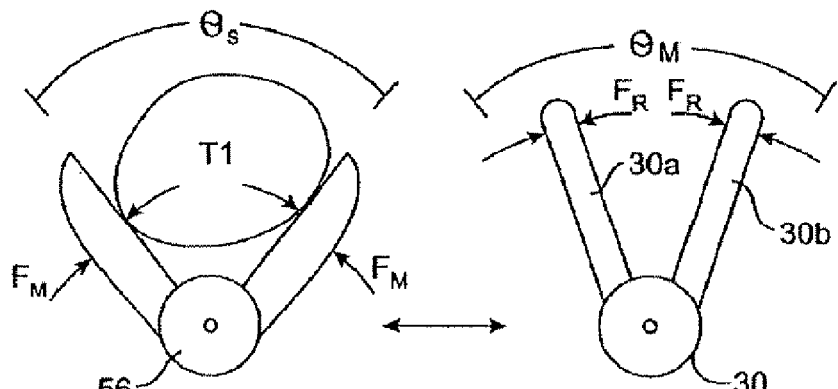
FIG. 9Aii
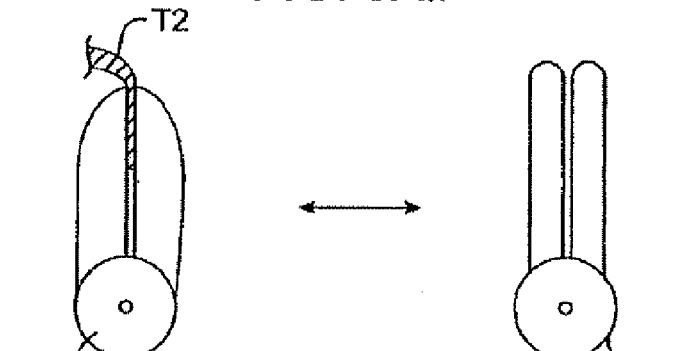
FIG. 9Aiii
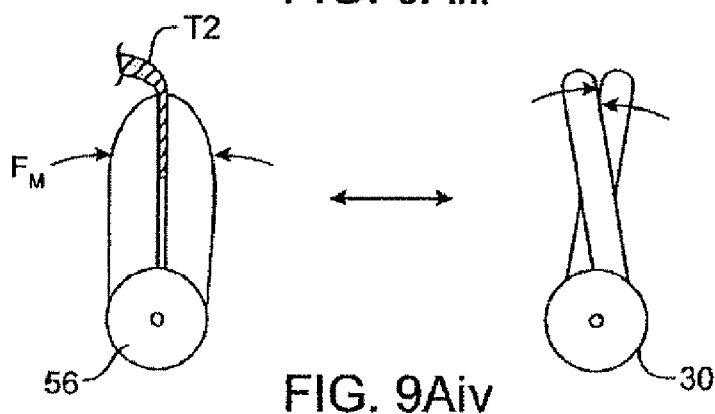
FIG. 9Aiv

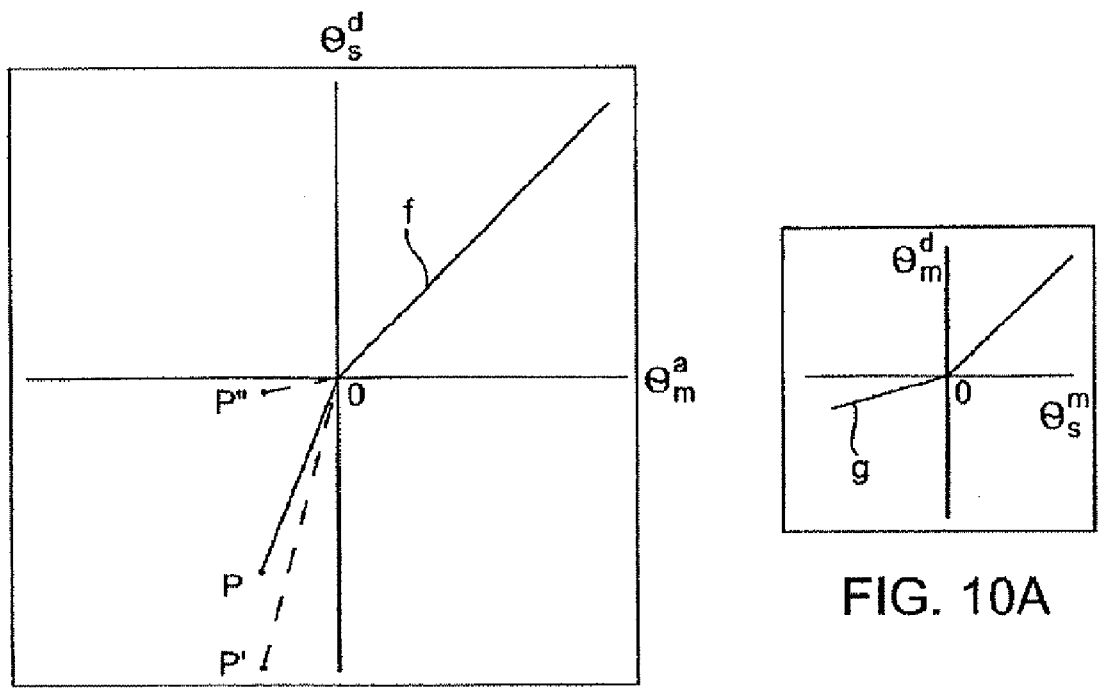
FIG. 10A
FIG. 10
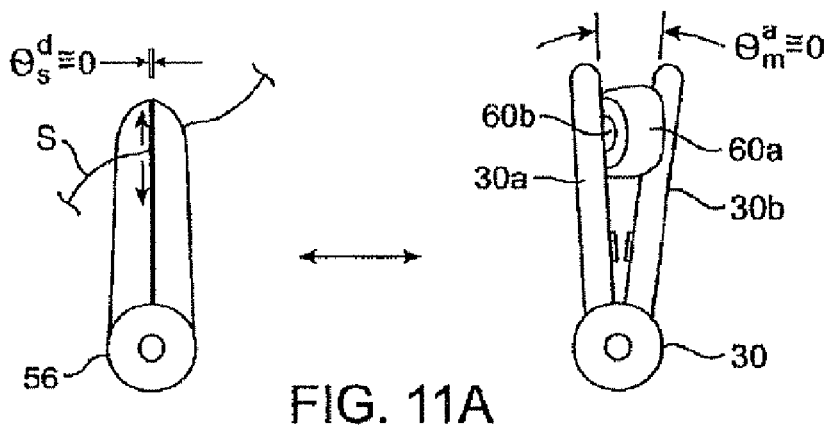
FIG. 11A
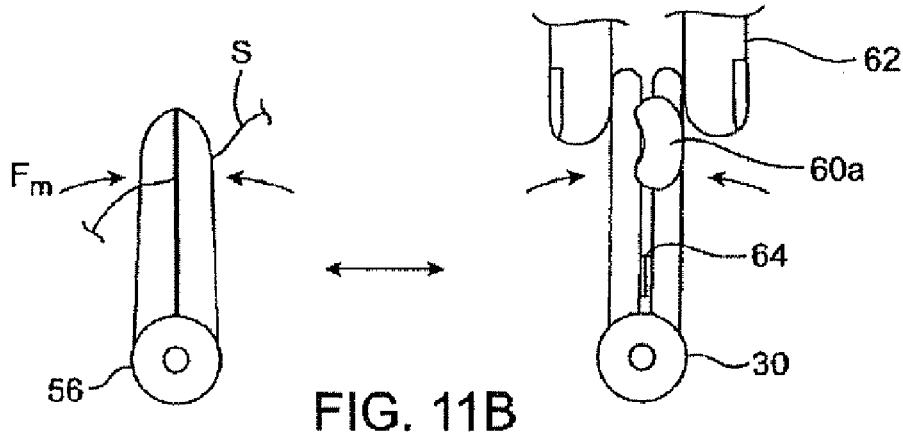
FIG. 11B

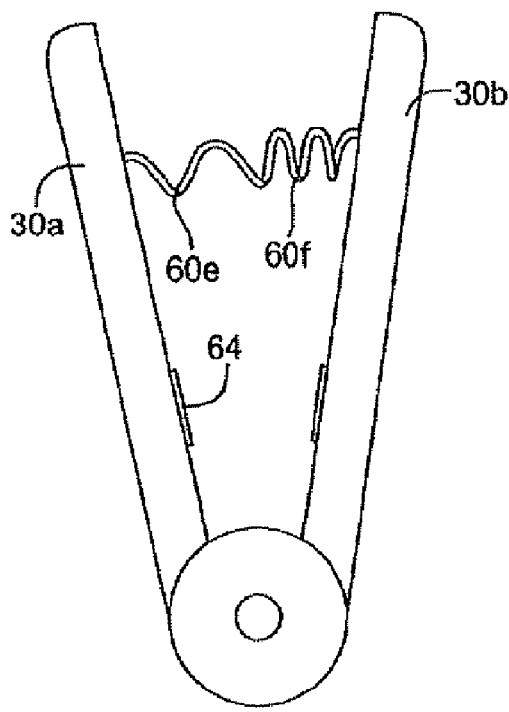
FIG. 11Di
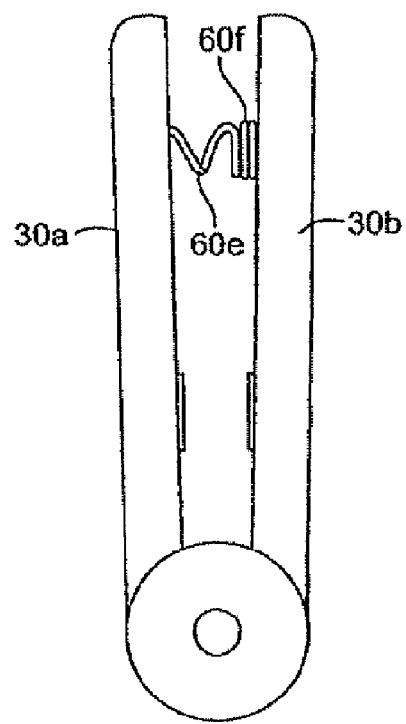
FIG. 11Dii
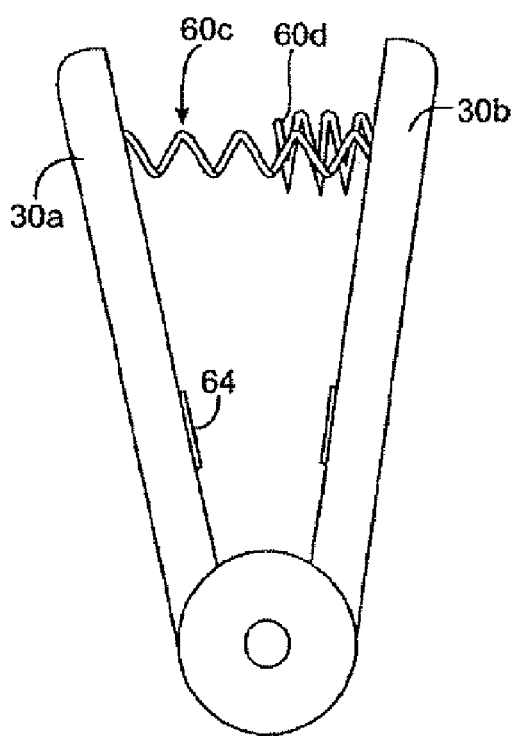
FIG. 11Ci
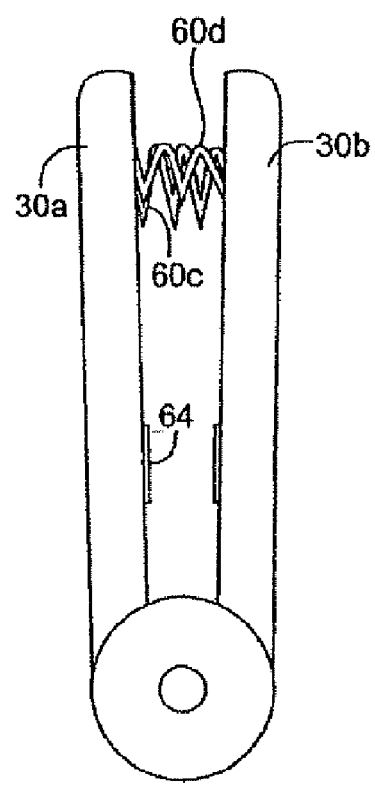
FIG. 11Cii

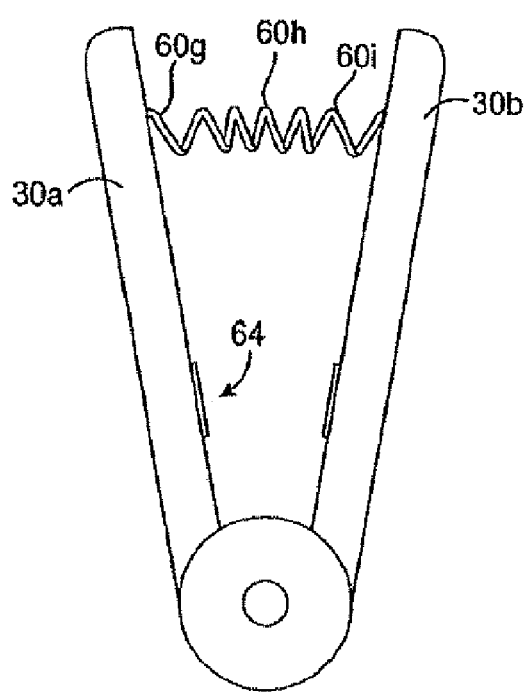
FIG. 11Ei
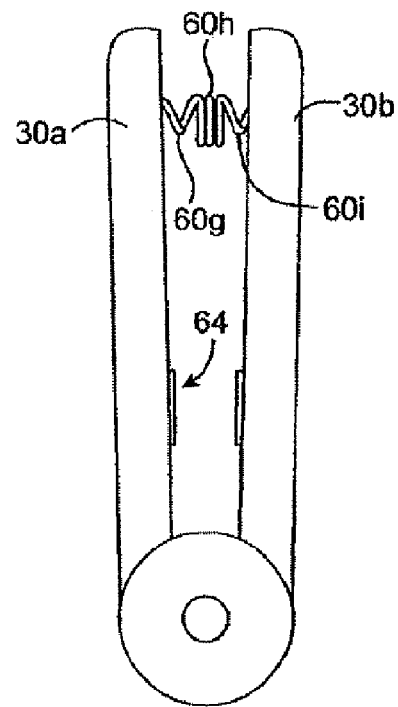
FIG. 11Eii
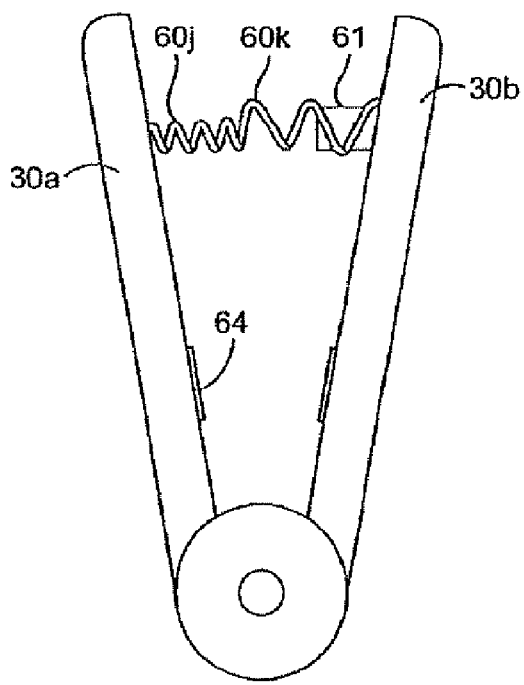
FIG. 11Fi
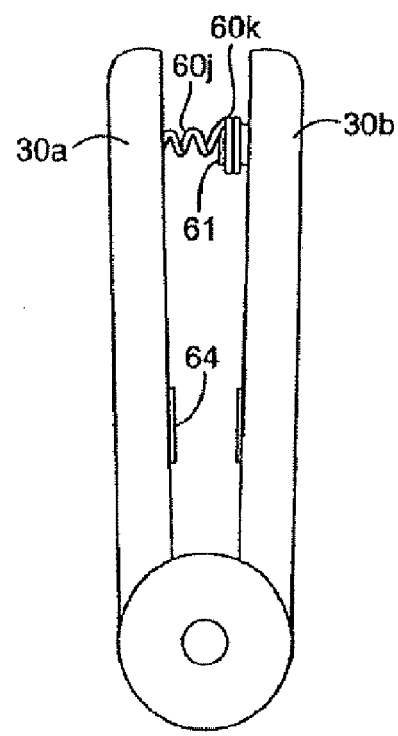
FIG. 11Fii

GRIP STRENGTH WITH TACTILE FEEDBACK FOR ROBOTIC SURGERY

CROSS-REFERENCE TO RELATED APPLICATIONS

This application is a continuation of U.S. application Ser. No. 11/074,372, filed Mar. 7, 2005, which is a continuation of U.S. application Ser. No. 10/437,771, filed May 13, 2003, now U.S. Pat. No. 6,879,880, which is a divisional of U.S. application Ser. No. 09/544,153, filed Apr. 6, 2000, now U.S. Pat. No. 6,594,552, which claims the benefit of U.S. Application No. 60/128,157, filed Apr. 7, 1999 under 37 C.F.R. §1.78, the full disclosures of which are incorporated herein by reference.

BACKGROUND OF THE INVENTION

The present invention is related to medical devices, systems, and methods, and is also relevant to robotic devices, systems, and methods for their use in medical and other robotic applications. In one embodiment, the invention provides a grip actuation system within a master/slave robot arrangement to give a system operator tactile feedback of grip strength when gripping small objects.

Minimally invasive surgical techniques are intended to reduce the amount of an extraneous tissue which is damaged during diagnostic or surgical procedures. By reducing the trauma to surrounding tissues, patient recovery time, discomfort, and deleterious side effects can be reduced. While many surgeries are performed each year in the United States, and although many of these surgeries could potentially be performed in a minimally invasive manner, only a relatively small percentage of surgeries currently use the new minimally invasive techniques now being developed. This may be in part due to limitations in minimally invasive surgical instruments and techniques, as well as the additional surgical training involved in mastering these techniques.

While known minimally invasive surgical techniques hold great promise, there are significant disadvantages which have, to date, limited the applications for these promising techniques. For example, the standard laparoscopic instruments used in many minimally invasive procedures do not provide the surgeon the flexibility of tool placement found in open surgery. Additionally, manipulation of delicate and sensitive tissues can be difficult while manipulating these long-handled tools from outside the body. Many surgical procedures are complicated by the limited access provided to the surgical site, in which tools and viewing scopes are often inserted through narrow cannulae, all while viewing the procedure in a monitor which is often positioned at a significantly different angle than the patient.

To overcome these disadvantages, minimally invasive telesurgical systems are now being developed. These systems will increase a surgeon's dexterity and effectiveness within constrained internal surgical sites. In a robotic surgery system, an image of the surgical site can be displayed adjacent master input devices. The system operator will manually manipulate these input devices, thereby controlling the motion of robotic surgical instruments. A servomechanism will generally move surgical end effectors in response to the operator's manipulation of the input devices, ideally providing translation, rotation, and grip actuation modes. As the servomechanism moves the surgical end effectors in response to movement of the input devices, the system operator retains control over the surgical procedure. The servomechanism may move the devices in position and orientation, and a processor of the servomechanism can transform the inputs from the system operator so that the end effector movements, as displayed to the system operator at the master control station, follow the position and orientation of the input devices as perceived by the system operator. This provides the system operator with a sense of "telepresence" at the internal surgical site.

The robotic surgical systems now being developed show tremendous promise for increasing the number and types of surgeries which may be performed in a minimally invasive manner. Nonetheless, these known systems could benefit from still further improvements. For example, although force feedback systems for robotic surgery have been proposed, the added cost and complexity of these proposed force feedback systems has often limited their implementation. Additionally, work in connection with the present invention has shown that known force reflecting master/slave robotic arrangements without force sensors may not be ideal for implementation of tactile feedback to the system operator in all the actuation modes within a telesurgical system, particularly in grip.

In light of the above, it would be desirable to provide improved surgical devices, systems, and methods. It would also be desirable to provide improved robotic devices, systems, and methods, both for use in robotic surgical systems and other robotic applications. It would be beneficial if these improvements enhanced the operator's control over, and tactile feedback from, the robotic end effectors. It would further be desirable if these improvements did not unnecessarily complicate the system, and if these improved techniques recognized differences between grip and other actuation modes that might justify specialized grip systems.

SUMMARY OF THE INVENTION

The present invention provides improved robotic devices, systems, and methods, particularly for use in telesurgical systems. In general, the invention provides an improved master/slave arrangement for enhanced telepresence, particularly for grip actuation within a multiple degree of freedom telepresence system. By applying the present invention, slave grip strength can be enhanced and/or tailored when master grip elements approach their closed configuration, rather than relying on gripping forces which are only a function of position error.

The invention provides an enhanced sense of feel by using a programmable grip strength amplification, generally without having to resort to slave force sensors. Instead, a grip error signal can be artificially altered beginning at a predetermined grip configuration. For example, where a grip input handle includes first and second grip members that move relative to each other to define a variable grip separation, and where an end effector similarly includes first and second elements defining a variable end effector separation, when above a predetermined grip separation, actuation of the grip members will preferably result in one-to-one corresponding actuation of end effector elements. This allows, for example, a robotic surgical system operator to change the separation angle of the jaws of a surgical forceps by corresponding changes to a separation angle of an input handle. In many embodiments, contact between the elements of the forceps may begin just as the gripping members pass the predetermined grip member separation (assuming the jaws are free to move with negligible tissue or other matter between the jaw elements). Continuing to squeeze the grip members beyond this predetermined point can quickly impose the maximum allowable gripping force on the jaws, thereby allowing the jaws to squeeze very small or thin objects such as sutures, tissue membranes, and the like, without having to push the grip members to an unnatural angle. In the exemplary embodiment, a biasing spring assembly may be provided between the grip members, with the grip members beginning to compress the spring assembly just as they pass the predetermined grip enhancement point. This provides tactile feedback to the robotic system operator indicating that the enhanced grip strength is being applied, and can simulate the resilient deflection of handles (such as the handles of a medical forceps or hemostat) felt when squeezing a small object using a traditional surgical tool.

In a first aspect, the invention provides a method comprising squeezing first and second grip members together with a hand of an operator. First and second end effector elements are moved in response to the squeezing of the grip members according to a control relationship. The control relationship is altered when the grip members are near a closed configuration.

The end effectors will often be moved by applying following forces in response to a misalignment between a grip separation (between grip members) and an end effector separation (between end effector elements). The separations may comprise angles, linear distances, vectors, or the like. In an exemplary embodiment, the moving step can be effected by measuring separations between the grip members and between the instrument elements. The end effector elements can then be moved by producing an error signal from a comparison between the measured grip separation and the measured instrument separation. The error signal will typically be enhanced when the grip members are adjacent a closed configuration. More specifically, the error signal may be enhanced by artificially altering the measured grip separation, preferably according to a continuous invertible function. By selecting a function which only alters the measured grip separation below a predetermined value, the end effector elements can follow the grip members with a one-to-one correspondence when the grip members are relatively wide open. In this relatively wide configuration, while it is generally desirable to have one-to-one following when no forces are applied against the end effectors, it may be acceptable to have significant angular misalignment (for example) between the grip members and the end effector elements when imposing high gripping forces. However, by increasing the sensitivity of the system to misalignment (and hence the grip strength) once the grip members come closer together, the instrument elements can apply the maximum gripping forces against a very small gripped object (such as a suture) without requiring the system operator to push the gripping elements together to an unnatural "overclosed" configuration.

Tactile feedback to the system operator of the altered gripping forces may be provided by driving the gripping members in response to the member/element misalignment using a reciprocal master/slave arrangement, and by altering the master error signal when the slave is nearer the closed position, ideally so as to provide a servo-mechanism with overall stiffness matching that of a desired tool. Alternatively, a simple feed forward system can provide tactile feedback to the operator by including a biasing mechanism in the gripping structure. This biasing mechanism can impose different reactive forces against the operator's hand beginning at the predetermined force enhancement point or biasing transition point.

In another aspect, the invention provides a robotic system comprising a master controller having a biasing system and first and second grip members defining a grip separation. The biasing system urges the grip members apart (typically with a varying force) so as to define a predetermined grip separation. A slave has first and second end effector elements, and defines an end effector separation therebetween. A servomechanism couples the end effector elements to the grip elements and applies a following force to the end effector elements. The servomechanism applies a first following force when the grip is wider than the predetermined separation, and a second following force when narrower than the predetermined grip separation. The biasing system thereby provides tactile feedback to the operator of a change in grip strength. In some embodiments, the biasing system comprises a variable rate spring which provides a varied tactile feedback at a biasing transition point.

The master controller will often be moveable with a plurality of positional and/or orientational degrees of freedom. The servomechanism may move the slave in a corresponding plurality of degrees of freedom in response to the positional and/or orientational movement of the master. In many embodiments, the positional and orientational force rates imposed by the servomechanism may remain substantially uniform throughout positional and orientational ranges of motion, the forces typically being based on the master/slave misalignment, or positional and orientational difference between the master and slave. In other words, the enhanced grip of the present invention may be specifically applied to actuation in the gripping mode.

The separation between the grip members and/or end effector elements will often comprise angular openings, although they may alternatively comprise linear separations between parallelogram linkages, or the like. These enhanced grip force techniques are particularly useful for actuating the jaws of surgical instruments such as forceps, scissors, clip appliers, clamps, or the like. Advantageously, the system may be capable of applying enhanced following forces which are tailored to the strengths and/or intended uses of these differing surgical tools, allowing these differing end effectors to be detached and sequentially secured to the servomechanism without having to alter the master controller.

In yet another aspect, the invention provides a robotic system comprising a master controller producing a master position signal in response to a position of the master along a first degree of freedom. A slave end effector produces a slave position signal in response to a position of the end effector along a first degree of freedom. The slave has a constraint limiting movement in the first slave degree of freedom. The end effector moves in response to an error signal; The error signal is defined at least in part by a difference between the master position signal and the slave position signal. A processor couples the master to the slave. The processor enhances the error signal when the slave is adjacent the constraint.

In another aspect, the invention provides a surgical robotic system comprising a master controller having first and second grip members defining a grip separation. An end effector having first and second end effectors is coupled to an actuator such that actuation of the end effector decreases the end effector separation. A processor is operatively coupled to the master controller and to the actuator such that when the amount of end effector separation is above a certain separation value, a decrease in the grip separation of the master controller controls the amount of end effector separation. When the end effector separation reaches a certain separation value, a further decrease in the grip separation controls the amount of force applied by the end effector.

In yet another aspect, the present invention provides a surgical robotic system comprising a master controller having first and second grip members that define a grip separation. An end effector having first and second end effectors and an end effector separation between the first and second end effectors is coupled to an actuator such that actuation of the end effector decreases the end effector separation. A processor is operatively coupled to the master controller and to the actuator such that when the end effector separation is above a certain separation value, a decrease of the grip separation of the master controller controls the amount of end effector separation. Upon the grip separation reaching a certain separation value, a further decrease of the grip separation controls the amount of force applied by the end effector.

Other objects, features, and advantages of the present invention will become apparent upon consideration of the following detailed description and the accompanying drawings.

BRIEF DESCRIPTION OF THE DRAWINGS

FIGS. 8A through F are perspective views of a variety of alternative end effectors for the tool of FIG. 7.

FIG. 9Ai through 9Aiv schematically illustrate master/slave following forces applied to grip different size objects.

FIG. 10 graphically illustrates a function for artificially enhancing an error signal when the grip members are below a predetermined position.

FIG. 10A graphically illustrates a function for enhancing tactile feedback using the reciprocal master/slave arrangement of FIG. 9B.

FIGS. 11A through 11B schematically illustrate the use and design of a biasing system to provide tactile feedback of an enhanced grip actuation force.

FIGS. 11Ci and 11Cii illustrate the biasing system having two springs for providing tactile feedback of an enhanced grip actuation force.

FIGS. 11Di and 11Dii illustrate the biasing system having a variable rate spring for providing tactile feedback of an enhanced grip actuation force.

FIGS. 11Ei and 11Eii illustrate an alternative biasing system having a variable rate spring for providing tactile feedback of an enhanced grip actuation force.

FIGS. 11Fi and 11Fii illustrate yet another biasing system having a variable rate spring for providing tactile feedback of an enhanced grip actuation force.

DESCRIPTION OF THE SPECIFIC EMBODIMENTS

Figure 1:
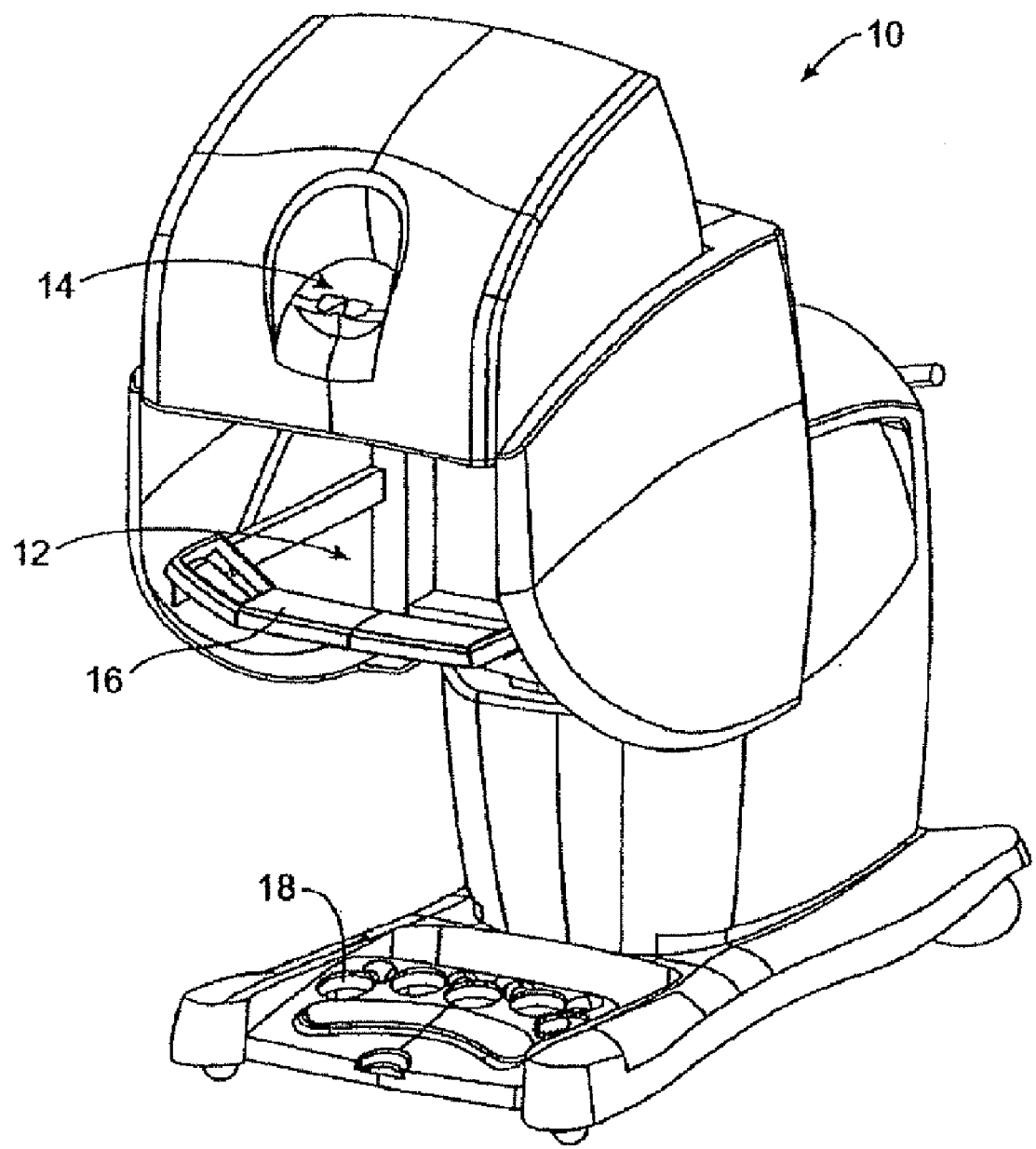
FIG. 1 is a perspective view of a master controller workstation according to the principles of the present invention.

This application is related to the following patents and patent applications, the full disclosures of which are incorporated herein by reference: PCT International Application No. PCT/US98/19508, entitled "Robotic Apparatus", filed on Sep. 18, 1998, U.S. application Ser. No. 09/418,726, entitled "Surgical Robotic Tools, Data Architecture, and Use", filed on Dec. 6, 1999; U.S. application Ser. No. 09/398,507, entitled "Master Having Redundant Degrees of Freedom", filed Sep. 17, 1999, U.S. application Ser. No. 09/457,406, entitled "Image Shifting Apparatus & Method for a Telerobotic System", filed on Dec. 7, 1999; U.S. application Ser. No. 09/378,173 entitled "Stereo Imaging System for Use in Telerobotic Systems", filed on Aug. 20, 1999; and U.S. Pat. No. 5,808,665, entitled "Endoscopic Surgical Instrument and Method for Use", issued on Sep. 15, 1998; the full disclosures of which are incorporated herein by reference.

The present invention provides improved robotic and surgery devices, systems and methods. The invention will find application in a wide variety of robotic systems, particularly those which include master/slave arrangements. The techniques of the present invention allow an operator to control the angle (or other separation measurement) between end effector elements by manually gripping an input device so as to vary the angle (or other separation measurement) between the input members. Advantageously, the invention allows a standard input device to drive a variety of end effector jaws, providing both a one-to-one angular correspondence throughout much of the travel and a programmable following force when the jaws are in a closed configuration, without having to over actuate the gripping members to an unnatural angle. The invention may also find applications for actuation in other modes in which motion of the slave is constrained, for example, movement of a single pinching element against a static structure. In other words, the invention may find application in providing enhanced telepresence for manufacturing, operation in hazardous environments such as nuclear power plants, chemical or biochemical processing, mining, or other robotic applications. Nonetheless, the invention will find its most immediate application to enhance robotic assisted surgery or telesurgery, in which the system operator manipulates tissues at an internal surgical site from outside the body.

The following preferred embodiments generally describe a master-slave relationship in which slave actuation is controlled by a master controller. For a portion of the actuation range of the slave (e.g., end effectors), the slave's position is controlled by the master controller with substantially no change in applied force. At a certain point, whether a predetermined threshold position of the master or slave or a sensed position of the slave against an object, the master slave control regime can shift from position control (or following control)

to force control, in which the force applied by the slave increases in response to further actuation of the master without substantially changing the position of the slave.

Referring now to FIG. 1, an exemplary surgical workstation 10 includes workspace 12 disposed adjacent a display 14. In this embodiment, the display comprises a binocular stereoscopic viewing system which superimposes a view of the internal surgical site (taken through an endoscope) over workspace 12. The surgeon or other system operator manually manipulates input devices by moving and repositioning input devices within workspace 12. In addition to the primary master control input devices moveably supported within workspace 12, workstation 10 may include buttons mounted on support 16, foot pedals 18, voice recognition input microphones, or the like.

Workstation 10 can house a processor that interprets the inputs from the system operator and provides signals directing movement of the surgical end effectors. Preferably, the processor maintains registration between the position and orientation of the master controller moving within workspace 12 and the end effectors as displayed by display 14, as described in U.S. Pat. No. 5,808,665, the full disclosure of which is incorporated herein by reference. Although registration between the master input controllers and the images of the end effector shown in display 14 enhances the operator's control and dexterity during delicate procedures, the present invention encompasses systems in which the display is offset from workspace 12.

Figure 2:
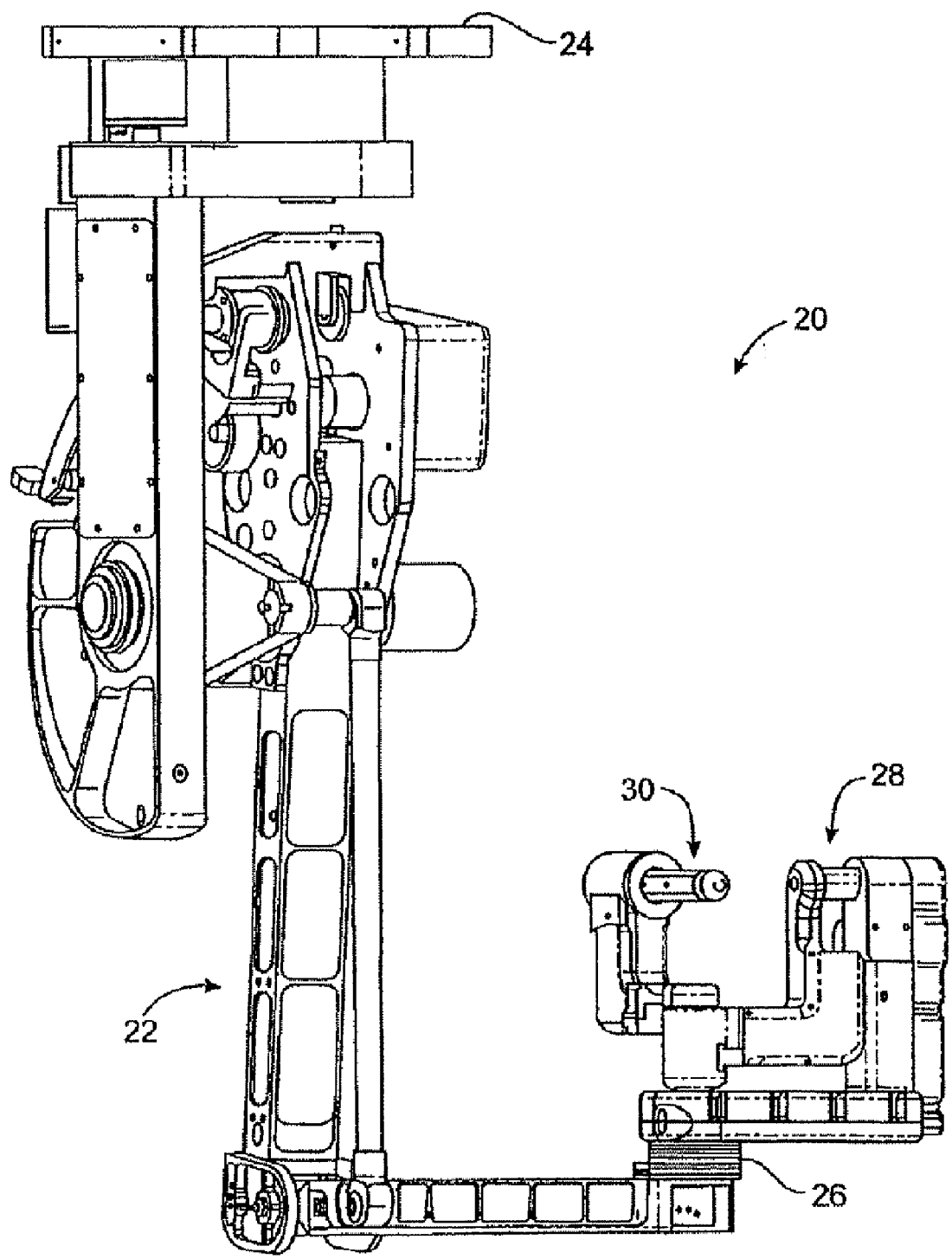
FIG. 2 is a front view of a master controller input device for use in the workstation of FIG. 1.

A master control input device 20 for use in workspace 12 is illustrated in FIG. 2. For understanding the present invention, master controller 20 may be considered to generally include three components. First, an arm 22 has a base 24 which is mounted to a housing of workstation 10. Arm 22 includes a series of linkages coupled by joints allowing a platform 26 of the arm to move in the three-dimensional workspace 12. In other words, arm 22 moves with three positional degrees of freedom, allowing the system operator to position a surgical end effector.

The second major component of the master input device 20 is a gimbal assembly 28. The gimbal assembly is mounted to platform 26, and supports an input handle 30 having first and second grip members 30a, 30b. Gimbal 28 generally accommodates changes in orientation of handle 30 with three orientational degrees of freedom.

Handle 30, and in particular, gripping members 30a and 30b (see FIG. 3) represent the third major component of master input device 20. In the exemplary embodiment, motors of arm 22 and gimbal 28 are capable of actively applying positional and orientational forces to handle 30, thereby providing tactile feedback to the operator using a reciprocal master/slave arrangement as described hereinbelow.

Figure 3:
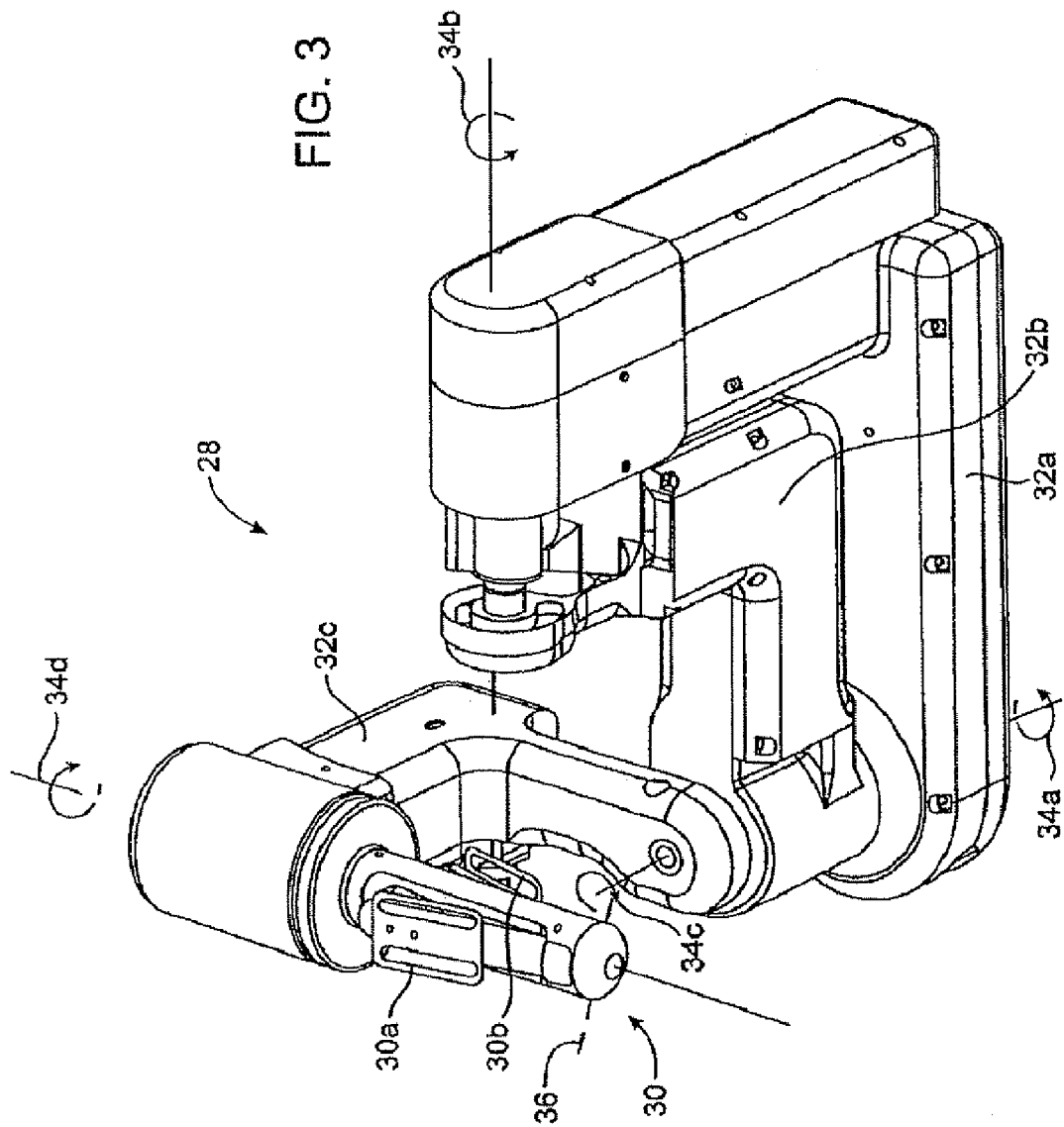
FIG. 3 is a perspective view of a gimbal supporting and providing orientational degrees of freedom to first and second grip members of the input device illustrated in FIG. 2.

Gimbal 28 and handle 30 are illustrated more clearly in FIG. 3. In this exemplary embodiment, gimbal 28 includes links 32a, 32b, and 32c. Gimbal 28 is mounted to platform 26 so as to rotate about axis 34a, and links 32 define additional axes 34b and 34c. Handle 30 is mounted to gimbal 28 by yet another actively driven joint for motion about axis 34d. Hence, gimbal 28 provides four driven orientational degrees of freedom, including a redundant orientational degree of freedom. Gimbal 28, arm 22, and the driving motors for these joints are described in more detail in co-pending U.S. patent application Ser. No. 09/398,507, entitled "Master Having Redundant Degrees of Freedom", filed Sep. 17, 1999, the full disclosure of which was previously incorporated by reference.

Unlike the joints of gimbal 28 and arm 22, grip members 30a and 30b of handle 30 pivot passively about an axis 36 with no drive motor provided for feedback from the slave. In the exemplary embodiment, a Hall effect transducer is mounted in one of the grip members and a magnet is mounted in the other, so that handle 30 generates a grip signal indicating the angular separation between grip members 30a and 30b. A biasing system urges the grip members apart, and the grip members may include loops of Velcro™ or the like to more firmly position the gripping members relative to a thumb and finger of the system operator. A wide variety of grip member structures might be used within the scope of the invention, including any surgical instrument handles, optionally including rigid or flexible loops for the thumb and/or fingers.

Figure 4:
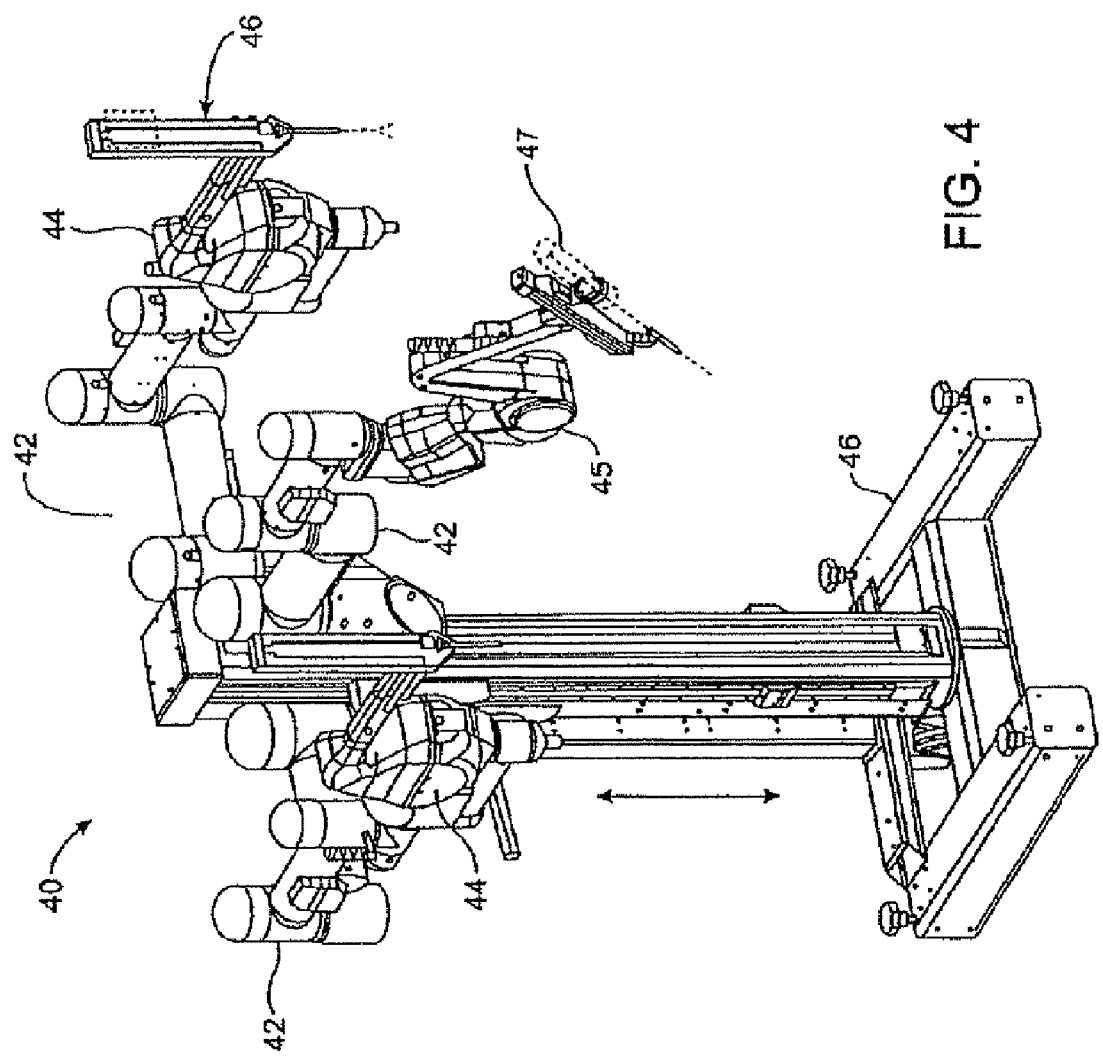
FIG. 4 is a patient side robotic surgical slave including first and second robotic arms for first and second surgical tools and a third arm for an endoscope, for use with the workstation of FIG. 1.

An exemplary embodiment of a patient-side robotic slave assembly is illustrated in FIG. 4. A patient-side cart 40 here includes three independent set-up joints 42 supporting robotic manipulators 44 relative to a base 46. Set-up joints 42 include arms which move vertically and horizontally to position manipulators 44 relative to the patient. Set-up joints 42 further include orientational degrees of freedom for orienting the manipulators. The set-ups joints will generally be manually positioned and then locked during manipulation of tissue.

Figure 5:
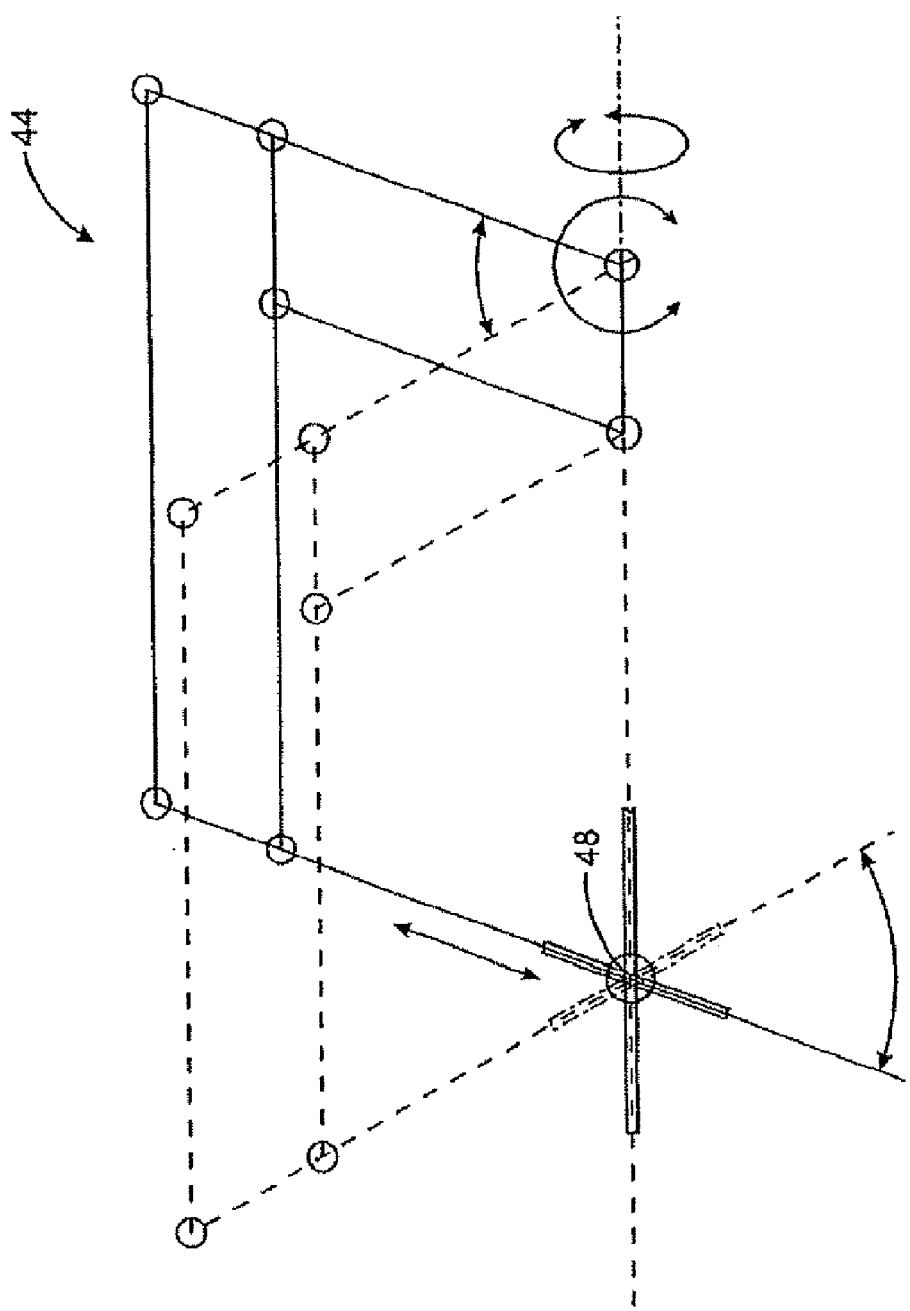
FIG. 5 schematically illustrates a parallelogram linkage providing a remote center of spherical rotation using the slave of FIG. 4.
Figure 6:
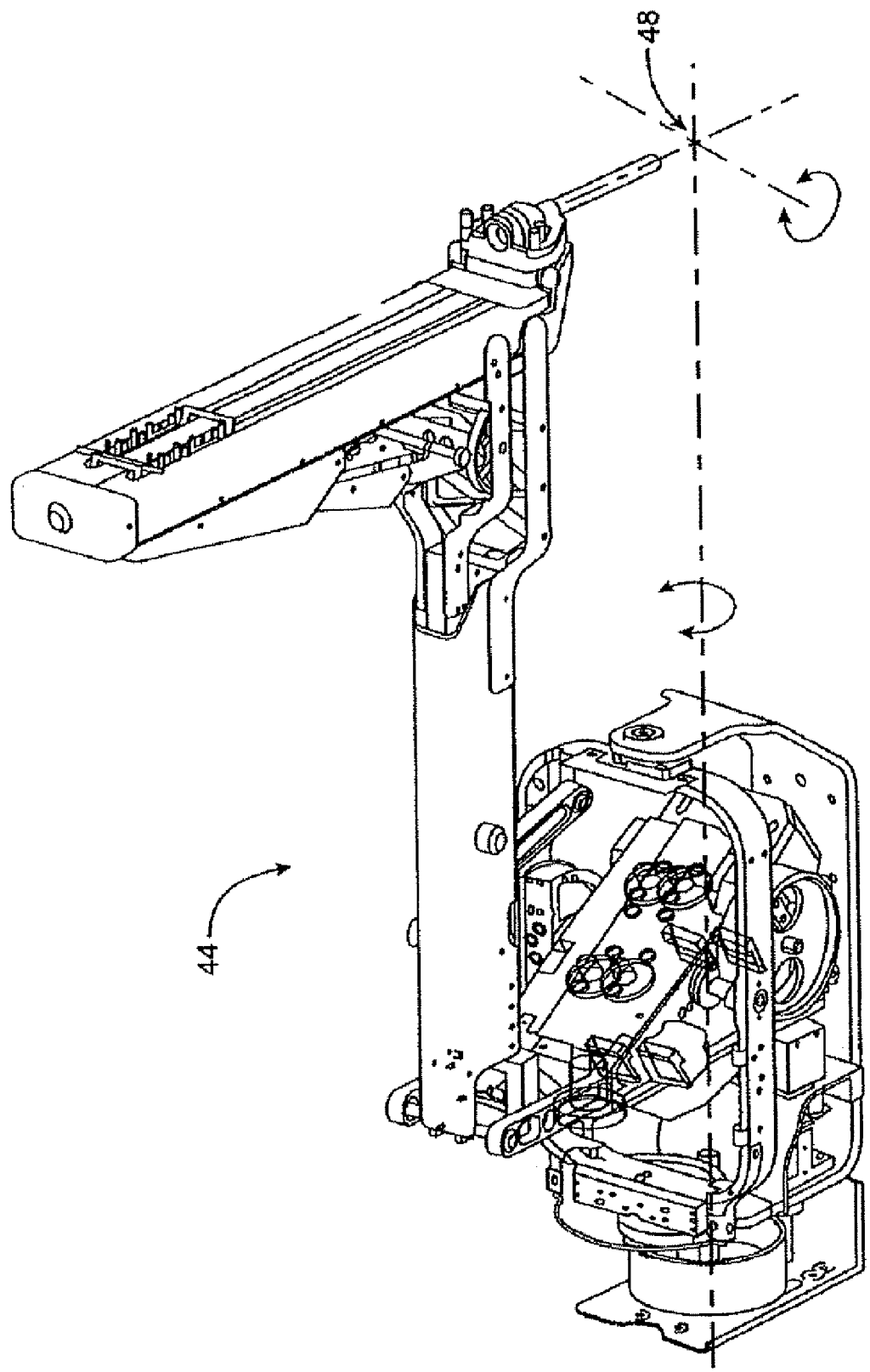
FIG. 6 is a perspective view of a surgical manipulator incorporating the linkage of FIG. 5 for use in the robotic slave of FIG. 4.

The use and structure of manipulators 44 can be understood with reference to FIGS. 4 through 6. Manipulators 44 move surgical tools 46 (see FIG. 7) about a fixed location or remote center of spherical rotation 48 using a parallelogram linkage arrangement. Remote center 48 remains at a fixed location relative to a base of the manipulator. By aligning remote center 48 with a cannula or other small axis point into an internal surgical site, and by mounting tool 46 onto manipulator 44 so that the tool can slide along shaft 50 of the tool, the manipulator can position a distal end 52 of the tool within the internal surgical site with three positional degrees of freedom. The use and structure of manipulator 44 is further explained in U.S. Pat. No. 5,800,423, the full disclosure of which is incorporated herein by reference.

While a manipulator 44 providing a remote center of rotation is included in the preferred embodiment of the present invention, it should be understood that a wide variety of alternative robotic arms and actuation mechanisms might be provided. For example, a slightly different manipulator 45 supports endoscope 47 in the slave system illustrated in FIG. 4. Endoscope manipulator 45 need not include actuation motors for actuation of the wrist and end effector elements. Still further alternatives are possible, including systems making use of a natural center, a passive joint which allows rotation about the cannula through the abdominal wall, as illustrated in the U.S. Pat. No. 5,184,601, the full disclosure of which is incorporated herein by reference.

Figure 7:
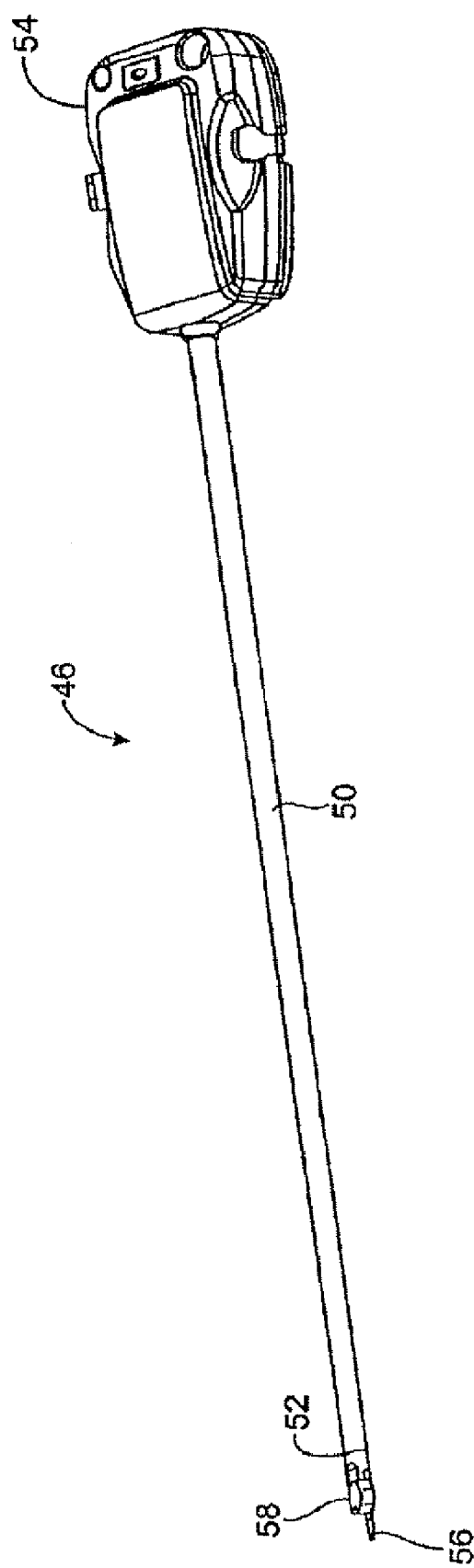
FIG. 7 is an endoscopic tool for use by the slave of FIG. 4.

An exemplary robotic surgical tool is illustrated in FIG. 7. Tools 46 includes a proximal housing 54 which interfaces with manipulator 44. Housing 54 includes mechanical interface elements for actuation of a surgical end effector 56 using motors mounted on the manipulator and cables extending along shaft 50. End effector 56 is coupled to distal end 52 of shaft 50 by a wrist 58. Preferably, wrist 58 provides at least two degrees of freedom, while shaft 50 is rotatable about its axis relative to housing 54, thereby providing three orientational degrees of freedom for surgical end effector 56 within the internal surgical site.

A variety of alternative end effectors for alternative tools are illustrated in FIGS. 8A through 8F. Several of these end effectors, including DeBakey forceps 56$i$, microforceps 56$ii$, Potts scissors 56$iii$, and clip applier 56$iv$ include first and second end effector elements 56a, 56b which pivot relative to each other so as to define a pair of end effector jaws. Other end effectors, including scalpel 56v and electrocautery probe 56vi have a single end effector element. While the varying actuation force of the present invention may find applications with end effectors having a single element, particularly where the element will be used at or near a constraint of movement of the element, the enhanced following forces of the present invention are particularly advantageous for use with end effectors defined by multiple end effector elements. In some embodiments, the tools or end effectors can be recognized by the system through reading of a memory mounted on the tool. make use of a memory structure mounted on the tool. The memory can perform a number of important functions when the tool is loaded on the tool manipulator. First, the memory can provide a signal verifying that the tool is compatible with that particular robotic system. Second, the tool memory may identify the tool-type (whether it is a scalpel, needle grasper, jaws, scissors, clip applier, electrocartery blade, or the like) to the robotic system so that the robotic system can reconfigure its programming to take full advantage of the tools' specialized capabilities. Exemplary surgical robotic tools, tool/manipulator interface structures, and data transfer between the tools and servomechanism is more fully described in U.S. patent application Ser. No. 09/418,726, entitled "Surgical Robotic Tools, Data Architecture, and Use", filed on Dec. 6, 1999, the full disclosure of which was previously incorporated by reference.

Figure 9A:
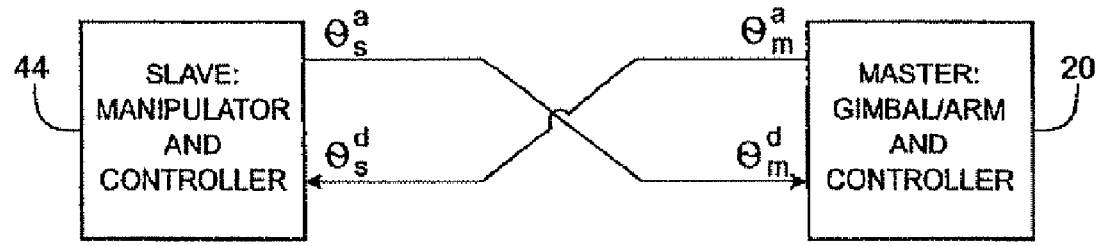
FIG. 9A is a functional block diagram schematically illustrating a master/slave arrangement for manipulating the position and orientation of robotic end effectors.

Referring now to FIG. 9A, a reciprocal master/slave arrangement is used for actuation of manipulator 44 to provide orientation and positioning of end effector 56 in response to movement of handle 30 of the input controller 20. It should be understood that the various master and slave positions θ may comprise vectors (in Cartesian space, polar space, joint space, or the like) as well as simple angles or linear separations, and the kinematic chains of the master and slave may be quite different, often even having different degrees of freedom. To provide force feedback to the operator, the master input device is actively driven by its motors toward alignment with the position occupied by slave 44. The amount of following force applied by the operator on the slave (and the reciprocal feedback on the operator's hand) are a function of a misalignment between a position (and orientation) of the master input device and a position (and orientation) of the slave end effector.

As illustrated schematically in FIG. 9A, master input device 20 defines an actual master position $\theta_m{}^a$. This actual position of the master is fed into the slave portion of the controller as a desired slave position $\theta_s{}^d$. The amount of force applied by the end effectors of the slave will vary with the difference between the desired position of the slave $\theta_s{}^d$ and the actual position of the slave $\theta_s{}^a$, with the following force on the end effectors increasing with increasing misalignment between the actual and desired positions, often with a proportional relationship.

To provide force feedback to the operator manipulating the master input device 20, the actual slave position $\theta_s{}^a$ is fed back into the motors of the input device as a desired master position $\theta_m{}^d$. Once again, the amount of force imposed by the motors of the master on the operator through the input device will vary with the misalignment or positional separation between the desired master position and the actual master position. This allows the operator to apply varying amounts of force through the servomechanism using the end effectors, and to have tactile feedback regarding the amount of force that has been applied.

It should be understood that the schematic representation provided in FIG. 9A of the servomechanism used to effect positional and orientational movement of the surgical end effector may appear quite different in its structural embodiment. For example, a single controller may be used to process both the master and slave signals. The controller can calculate error signals based on the difference between the actual and desired positions in space, and will generate servomotor torque controlling signals based on those error signals. As the master input controller and surgical end effector are moveable in a plurality of orientational and positional degrees of freedom, the calculation of these motor torques may involve vector coordinate transformations such as those described in more detail in copending U.S. patent application Ser. No. 09/373,678, filed Aug. 13, 1999, the full disclosure of which is incorporated herein by reference.

In general, the actual configuration of the master and slave will be measured using potentiometers, encoders, or other position, velocity, and/or acceleration sensors affixed to rotational joints of the input control devices and slave manipulator. Position information may also be provided by encoders and/or potentiometers affixed to the set-up joints 42, which may include both rotational joints and linear sliding joints (particularly for the vertical axis). A variety of alternative configuration input mechanisms might be used, including stepper motors, optical configuration recognition systems (for example, using light emitting diodes mounted to the surgical tools and a CCD/frame grabber optical processing system coupled to the endoscope), and the like. It should also be understood that this direct master/slave arrangement will often provide uniform following forces throughout the range of the motion of the master and/or slave, regardless of whether the following forces are applied using a system having a single degree of freedom, or a complex input control device and slave mechanism having six degrees of freedom for both the master and slave (optionally even including redundant degrees of freedom for the master and/or slave to avoid singularities).

While the reciprocal master/slave arrangement of FIG. 9A may be implemented to actuate end effector 56 in response to manipulation of handle 30 for gripping of objects between end effector elements 56a and 56b, the uniform following forces provided by this arrangement can have disadvantages which can be understood with reference to FIGS. 9Ai through 9Aiv. End effector 56 is first shown engaging a relatively large tissue T1 with no gripping force. The master position $\theta_m$ is equal to the slave position $\theta_s$. As there is no difference between the signals generated to measure these positions, the positional error signal, separation misalignment, and following forces are all zero.

Referring now to FIG. 9Aii, as the operator imposes squeezing forces on handle 30 to bring gripping members 30a, 30b closer together (and thereby reducing the separation angle), the servomechanism begins to apply the following forces against end effector 56. As the difference between the grip angle and end effector angle increases, the following forces imposed by the end effector elements against the large tissue T1 (and the reactive forces of the tissue against the end effector) increase. Eventually, the following forces reach a maximum $F_m$, which may be determined by a strength of the surgical tool, a limitation of the motor torque, or a limitation based on the intended uses of the tool (for example, to avoid severing of tissues with forceps). Regardless, the servomechanism will preferably limit the following forces before irreparable damage is inflicted on the robotic system.

To implement maximum following forces $F_m$, the operator has squeezed gripping members 30a, 30b well beyond the separation angle between the end effector elements. While it is generally preferable to maintain a one-to-one correlation between the angles of the gripping members and end effector elements, having a significant misalignment to effect the maximum following forces is generally acceptable when the separation angle of the gripping members remains significantly above zero when the maximum following force $F_m$ is imposed. Optionally, handle 30 may impose reciprocal forces $F_r$ against the hand of the operator to provide a tactile indication of the strength with which thick tissue T1 is being gripped to the operator.

As illustrated in FIGS. 9Aiii and 9Aiv, the situation is less acceptable when a thin tissue T2 of negligible thickness is gripped. When just engaging the tissue with the elements of end effector 56, the gripping members of handle 30 again define a separation angle that is substantially equal to the separation angle defined by the end effector elements. However, as this gripping configuration provides a quite small angular separation between the gripping members, imposition of maximum following forces $F_m$ against small tissue T2 only results when the gripping members are pushed beyond each other to define a negative gripping angle. This unnatural gripping actuation detracts from the operator's ability to accurately control the end effectors, particularly during delicate telepresence procedures involving the gripping of small objects, such as sutures, needles, and small tissues during telesurgery.

Figure 9B:
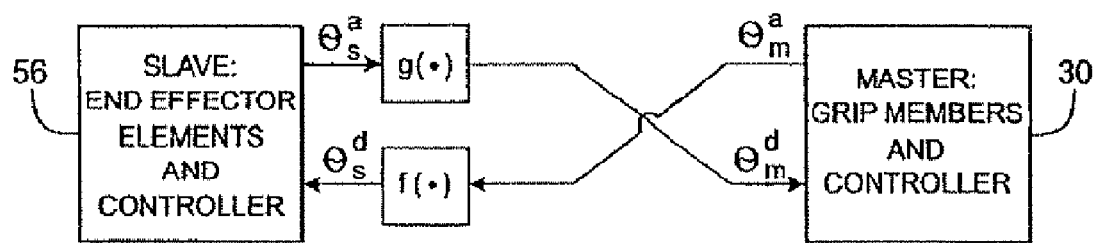
FIG. 9B is a functional block diagram schematically illustrating a master/slave arrangement providing an enhanced grip strength according to the principles of the present invention, in which the master is driven so as to provide tactile feedback to the system operator of the enhanced grip forces.

Referring now to FIGS. 9B and 10A, an alternative servomechanism arrangement artificially alters the actual master position $\theta_m^a$ according to a function $f$ to derive a desired slave position $\theta_s^d$. Function $f$ takes the form $\theta_s^d = f(\theta_m^a)$, and is preferably an invertible (monotonic) and continuous function of the actual master position, optionally such as that illustrated in FIG. 10. Function $f$ artificially increases (or in some cases, may decrease) the calculated error signal once the grip separation drops below a predetermined point O. This effectively increases (or decreases) the motor torque signals sent from the controller to the motors of the slave. Examples of when it may be desired to decrease grip strength include the use of low strength delicate tools in which a very small misalignment can produce the maximum following force, so that there would be little tactile indication of grip without decreasing the slope of $f$.

To provide feedback to the operator in this reciprocal master/slave arrangement, the actual slave position $\theta_s^a$ may also be manipulated according to a function g: $\theta_m^d = g(\theta_s^a)$ to derive a desired master position $\theta_m^d$ from which the master motor torques can be calculated. Function g will preferably also comprise a continuous, invertible function. Where implemented, g may comprise a coupling of the lever arm of the master grip members, the particular end effector, and the compliance of the tool drive system, including the servomotor compliance and the tool transmission system. Preferably g will provide one-to-one actuation when open, will have the slave just closed when the master is just closed (shown as O), and will have a slope below the "just closed" point so that the restoring force applied against the operator's hand matches that of a conventional tool, thereby providing feedback to the operator accurately reflecting the enhanced forces provided when the end effector and handle are near their closed configurations.

As can be understood with reference to FIGS. 9B, 9Aiii, and 10, once the separation between the gripping members drops below a predetermined point (arbitrarily indicated at the origin O in FIG. 10) a small additional decrease in gripping member separation $\theta_m^a$ will result in a significantly larger change in the desired position of the slave $\theta_s^d$. Above the predetermined point, the actual master position and desired slave position can remain the same, thereby providing the greatest dexterity for the system operator's control over the end effector.

Figure 9C:
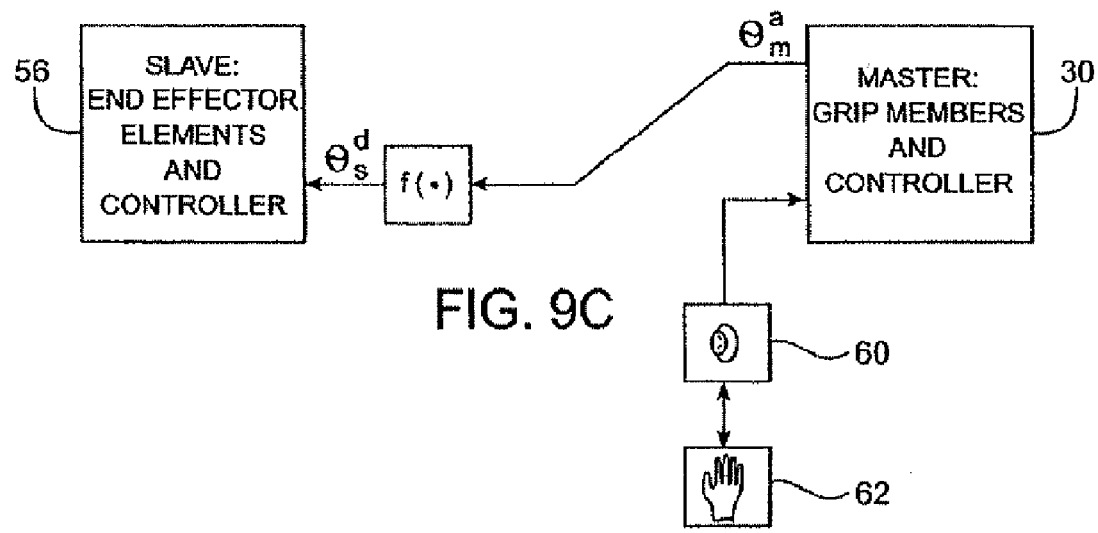
FIG. 9C is an alternative functional block diagram schematically illustrating an enhanced grip force master/slave arrangement in which the mechanical biasing mechanism provides tactile feedback to the system operator.

Referring now to FIG. 9C, an alternative servomechanism arrangement according to the principles of the present invention makes use of function $f$ to alter the actual position of the grip members so as to generate the desired position of the slave end effector, as described above. However, rather than relying on a reciprocal master/slave arrangement to provide feedback of the augmented end effector forces as the grip members and end effector elements approach their closed configuration, the system of FIG. 9C relies on a biasing system 60 which interacts with the operator's hand 62 to provide tactile feedback to the operator with a feed forward system, as can be understood with reference to FIGS. 10, and 11A to 11F.

Figure 10B:
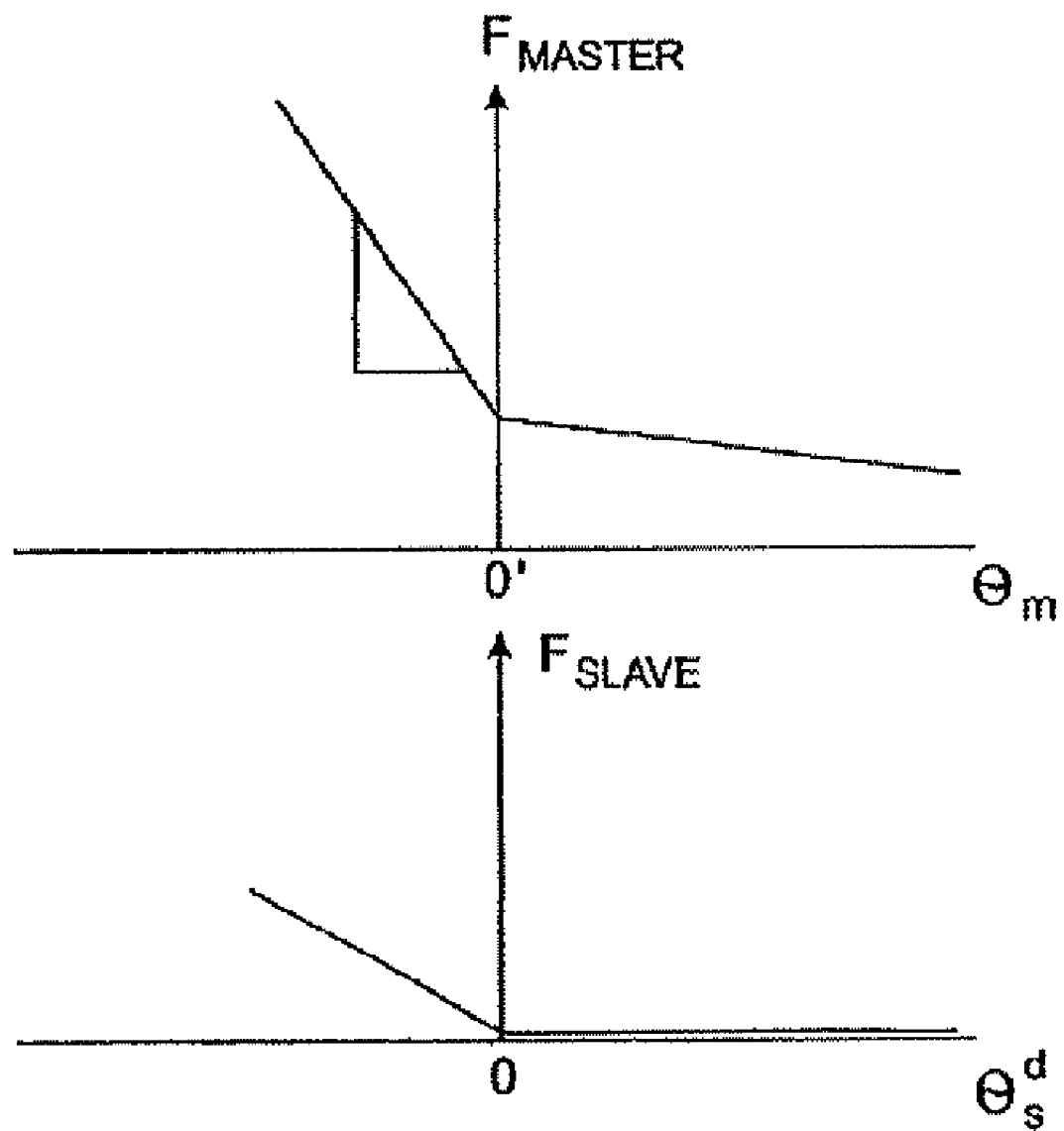
FIG. 10B graphically illustrates corresponding grip and end effector forces.

FIG. 11A illustrates end effector 56 just engaging a suture S but not yet applying significant forces against the suture. As the cross-sectional thickness of suture S is quite small, the separation between the end effector elements is effectively zero. As no forces are being imposed by the servomechanism, the grip separation angle of handle 30 is also substantially equal to zero. Note that the grip elements need not exactly define a zero angle. At this nominal position, grip elements 30a and 30b are just beginning to engage a biasing mechanism 60a of biasing system 60. Biasing mechanism 60a is here illustrated as a elastomeric bushing surrounding a grip return spring 60b. A variety of biasing structures might be used in place of biasing mechanism 60a, including springs, magnets, or the like. Ideally, the biasing mechanism will define a predetermined biasing transition point. As can be understood with reference to FIG. 10B, the force applied to the master F increases at predetermined master separation O'. This biasing system transition point will preferably occur just as the end effector elements touch, and will thereby indicate to the operator the enhanced grip strength being applied by the servomechanism. In FIG. 10B, the end effector grip force g is illustrated for corresponding grip actuation by the master when gripping an object of negligible thickness.

As illustrated in FIG. 11B, operator's hand 62 can squeeze handle 30 beyond the nominal zero angle by compressing bushing 60a between the grip members. Once the operator squeezes the handle sufficiently to engage stops 64 of the grip members, end effector 56 will preferably be imposing the maximum following force $F_m$ against suture S. This maximum gripping force configuration is designated by the point P along function $f$ illustrated in FIG. 10. Advantageously, the reactive forces provided by bushing 60a against operator's hand 62 provide tactile feedback to the operator of the enhanced following forces below the predetermined position. As described above, function $f$ preferably comprises the identity function above the predetermined position O. It should be understood that the predetermined position need not define any actual dimensions or forces. Where a maximum force $F_m$ is imposed beginning at a maximum force misalignment angle such as that illustrated in FIG. 9Aii, the predetermined point will preferably be within that maximum force misalignment angle from a fully closed configuration of handle 30 as defined by grip members 30a and 30b.

As shown in FIG. 11C, the biasing system may comprise two biasing springs to define the biasing transition point: a soft spring 60c which is easily compressed by the operator, and a stiff spring 60d. The stiff spring 60d may have a relaxed length which is less than a maximum grip separation, so that the stiff spring 60d does not impose any force when the grips 30a, 30b are in an open gripping range. The soft spring 60c has a relaxed length greater than the maximum separation, so that the soft spring 60c always provides a gentle return force to aid opening the grips 30a, 30b. When the grips 30a, 30b are closed to the predetermined biasing transition point, the stiff spring 60d (which may ride within or over the soft spring) engages the grip members 30a, 30b, and begins to add significantly to the return force. Hence, the grip motion range may be separated into a grip open range, a just closed point, and a squeezed grip range.

As shown in FIGS. 11D to 11F, the biasing system 60 may comprise a single variable rate spring 60. Because the two concentric springs of FIG. 11C can become tangled, a preferred embodiment of the biasing system comprises a variable rate spring formed from a single coil to indicate the biasing transition point to the user. In an embodiment illustrated in FIGS. 11Di and 11Dii, the variable rate spring 60 has two sections of spring which have a similar diameter. A first section 60e has coils that are spaced farther apart than the coils of a second section 60f. As shown in FIG. 11Dii, as the grips 30a, 30b are squeezed together, both sections of the coil 60e, 60f deflect a similar amount until the spring section in the second section 60f bottoms out at a "solid height." Consequently, any further squeezing of the grips 30a, 30b are biased only by the first section 60e and the resulting biasing spring rate is higher. Accordingly, the user is provided tactile feedback to indicate the biasing transition point.

In another embodiment shown in FIG. 11Eii and 11Eii, the variable rate spring 60 comprises three sections. A first section 60g and third section 60i have coils that are spaced farther apart than a second section 60h. As the grips 30a, 30b are squeezed together the grips are initially biased by all three sections 60g, 60h, 60i of the coil. When the grips 30a, 30b hit a point where second section 60h is fully compressed, (i.e. the biasing transition point) the grips will be biased by only the first and third section of the coil. The spring constant provided by the first section 60g and third section 60i of the coil provide tactile feedback to the operator of the enhanced following forces below the predetermined transition point.

Another embodiment of the biasing system 60 is illustrated in FIG. 11Fi and 11Fii. The variable rate spring 60 comprises a first section 60j which has a first diameter and a second section 60k which has a second, larger diameter. The first section and second section can have the same coil distance or a different coil difference. In most implementations, a spud 61 is positioned within the coils of the second section for guiding the coils and for acting as a stop for the smaller diameter spring 60j. Accordingly, when the grips 30a, 30b are squeezed together, the spring sections 60j, 60k compress until the second section compresses to the biasing transition point. At the biasing transition point, the spud 61 contacts the first section of the spring 61j and acts as a stop for the first section 61j to vary the spring rate and to provide tactile feedback to the user.

In general, a fully closed end effector configuration is defined by engagement between the end effector elements. This may occur just as the end effector elements come into contact, as in the case of forceps. Alternatively, this may occur after some sliding engagement between the end effector elements, as in the case of scissors. Advantageously, the reactive forces applied by biasing system 60 against the operator's hand 62 as the jaws gradually close harder and harder can substantially mimic the resilience provided by the mechanical deflection of open or endoscopic surgical handles, such as when a surgeon manually clamps or squeezes the handles together beyond the initial engagement of the standard end effector elements.

Referring once again to FIG. 10, the predetermined force enhancement initiation point O is determined by the configuration of handle 30 and biasing system 60. Similarly, the fully closed or "slammed" configuration of the handle is determined by stop 64 of the handle. Hence, the lateral position (corresponding to $\theta_m{}^a$) of points O and P will preferably remain unchanged for a variety of different end effectors when different tools are attached to a surgical robotic system. However, as noted above, the actual strengths and intended maximum forces of these different tools may be significantly different. To allow a variety of different tools to be used with the system, the processor of the servomechanism may revise function $f$ to an alternative maximum force position points P' or P''. This allows the servomechanism to adapt to a wide variety of tools without having to revise the mechanical configuration of the master controller when tools are changed. For example, the tools can make use of a chip or other memory structure mounted on the tool. The memory can provide a signal verifying that the tool is compatible with that particular robotic system or the tool memory may identify the tool-type (whether it is a scalpel, needle grasper, jaws, scissors, clip applier, electrocartery blade, or the like) to the robotic system so that the robotic system can reconfigure its programming to take full advantage of the tools' specialized capabilities.

It will be recognized that a wide variety of functions might be applied to enhance grip strength. In the exemplary embodiment, function $f$ comprises a linear function directly connecting the maximum force/slam point P with the predetermined force enhancement position O. This allows directly proportional control over the following forces of the slave, and can be substantially reproduced by a biasing structure to provide accurate tactile feedback. Alternatively, more complicated functions might be used. Preferably, the function will be continuous so as to avoid "jumps" in gripping force. Function $f$ will preferably be monotonic and invertible, particularly where force feedback is to be effected using a reciprocal master/slave system, as described above.

To accurately model the forces applied by the end effectors, it should be recognized that the slave position will often be measured remotely (at the motor/sensor location), rather than at the end effector joint. Hence, the compliance of the system will reflect the compliance of a portion of the transmission system. This can be accommodated using the formula $$F_S = \frac{K_{servo} * K_{mech}}{K_{servo} + K_{mech}} \theta_s^d$$

where $F_s$ is the end effector gripping force, $K_{servo}$ is the effective spring constant of the motor, and $K_{mech}$ is the spring constant of the mechanical transmission elements. This equation may allow the robotic system to mimic the stiffness of a particular tool when grip separation is at a minimum. Surgical tools often flex when fully squeezed. By properly compensating for the spring constant of the motor and mechanical transmission elements, the overall servomechanism can transition from a relationship determined from servomechanism design considerations (when wide open) to a surgical tool-like relationship (when clamped closed).

The signal processing used to provide the enhanced grip following forces described above is illustrated in more detail in FIG. 12. A Hall effect transducer 66, 68 measures the handle separation $\theta_m$ by sensing the distance between the transducer (which is mounted on grip member 30a) and a magnet (mounted on grip member 30b). The actual master grip separation $\theta_m{}^a$ is processed to provide the desired slave separation as described above. The actual slave separation $\theta_s{}^a$ (as measured by an encoder or potentiometer of motor 70) is subtracted from the desired slave separation $\theta_s^d$ to provide a slave error signal $e^s$. Optionally, the grip separation velocity $\dot{\theta}_m^a$ may also be modified according to function $f$, with the actual slave velocity $\dot{\theta}_s^a$ subtracted therefrom to provide a velocity error signal $\dot{e}_s$. The error signal and velocity error signal are amplified by associated factors, $K_p$ and $K_d$, respectively, and are added together to produce a motor torque signal $\tau$. Motor 70 produces a torque in response to torque signal $\tau$. While the preferred embodiments vary $\theta_s^d$ produce the motor torque signal $\tau$, it will be appreciated that instead of varying $\theta_s^d$, the $K_p$ and $K_d$ factors can be varied to produce the motor torque signal $\tau$.

The use of positional velocity and velocity error signals may help inhibit excessive cycling of the system as the slave attempts to follow the master. Hence, these velocity signals represent a viscosity of the system. Their use may not be necessary, particularly for effecting grip, in light of the small masses and high friction and grip forces that are involved. Once again, it should be understood that this illustration is a simplification. For example, two or more motors may be energized to provide following grip forces, often with a motor dedicated to each end effector element.

Figure 12:
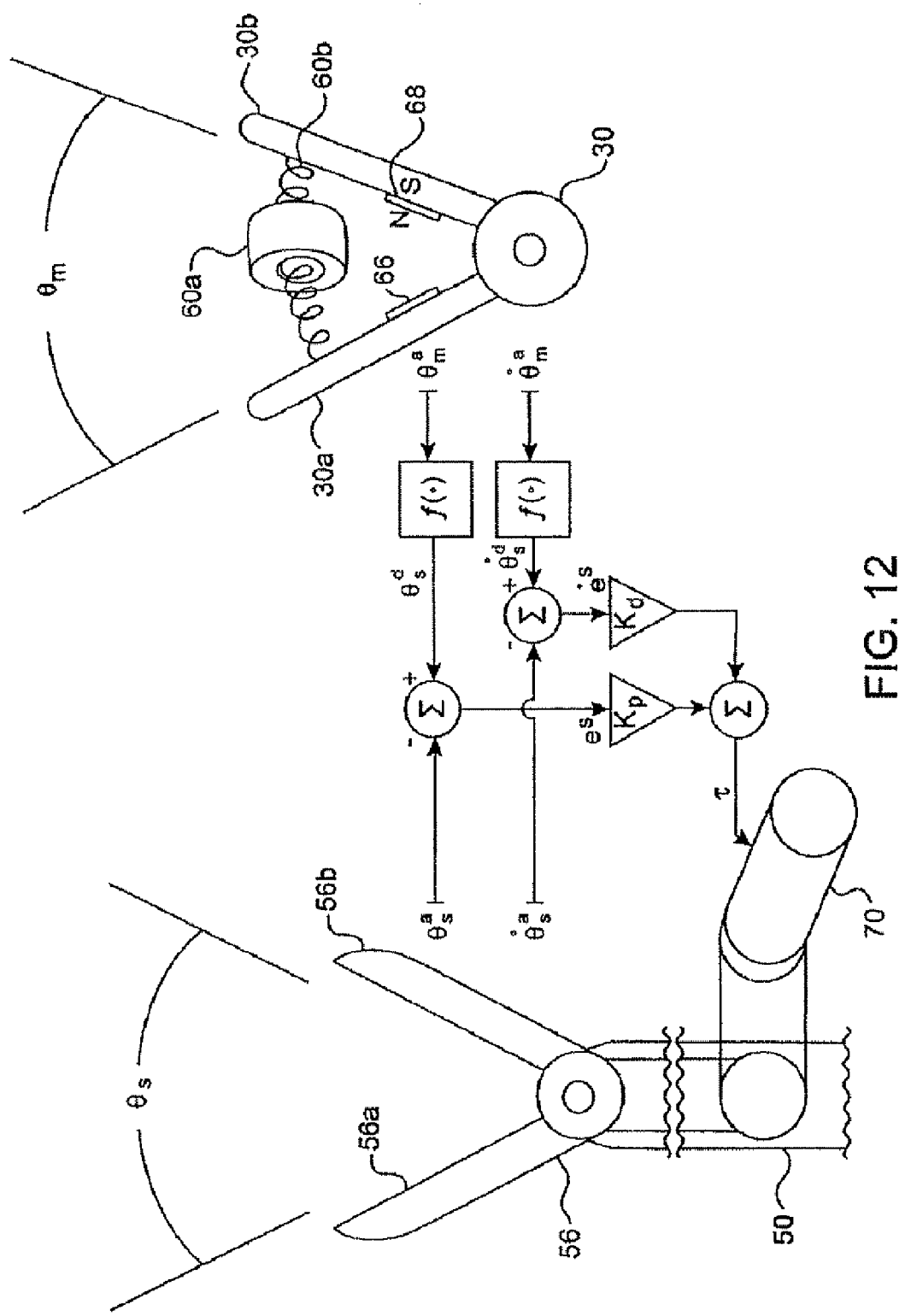
FIG. 12 schematically illustrates a master/slave control system according to the principles of the present invention.

The system of FIG. 12 enables the servomechanism to be designed so that it feels like a system having both position sensors in conjunction with force sensors to create the signals which are translated into forces under certain circumstances. The use of force sensors at the distal end of the slave mechanism can enable the designer to measure, and hence control, the force applied by the slave to the tissue. Additionally, the use of force sensor at the grip element of the master manipulator can enable the designer to measure, and hence command to the slave, the force being applied by the operator on the handle. The benefits of such a configuration are as follows: First, the master return springs are accurately modeled as linear. Second, the appropriate model for the force applied at the end effector is generated. Third, the objects being grasped are small compared to the range of motion of the slave grip (so that the grip enhancement can be enabled at the time when gripping should begin), and fourth, the restoring force from the master grip's return springs is a good model for what the user expects to feel using a conventional tool. Although the accuracy with which this last condition is met may not be exact when only one set of return springs is used for different tools with different allowed grip strengths a good approximation is created and many of the benefits of a full force sensing system are provided with this simple feed-forward system.

Figure 13A:
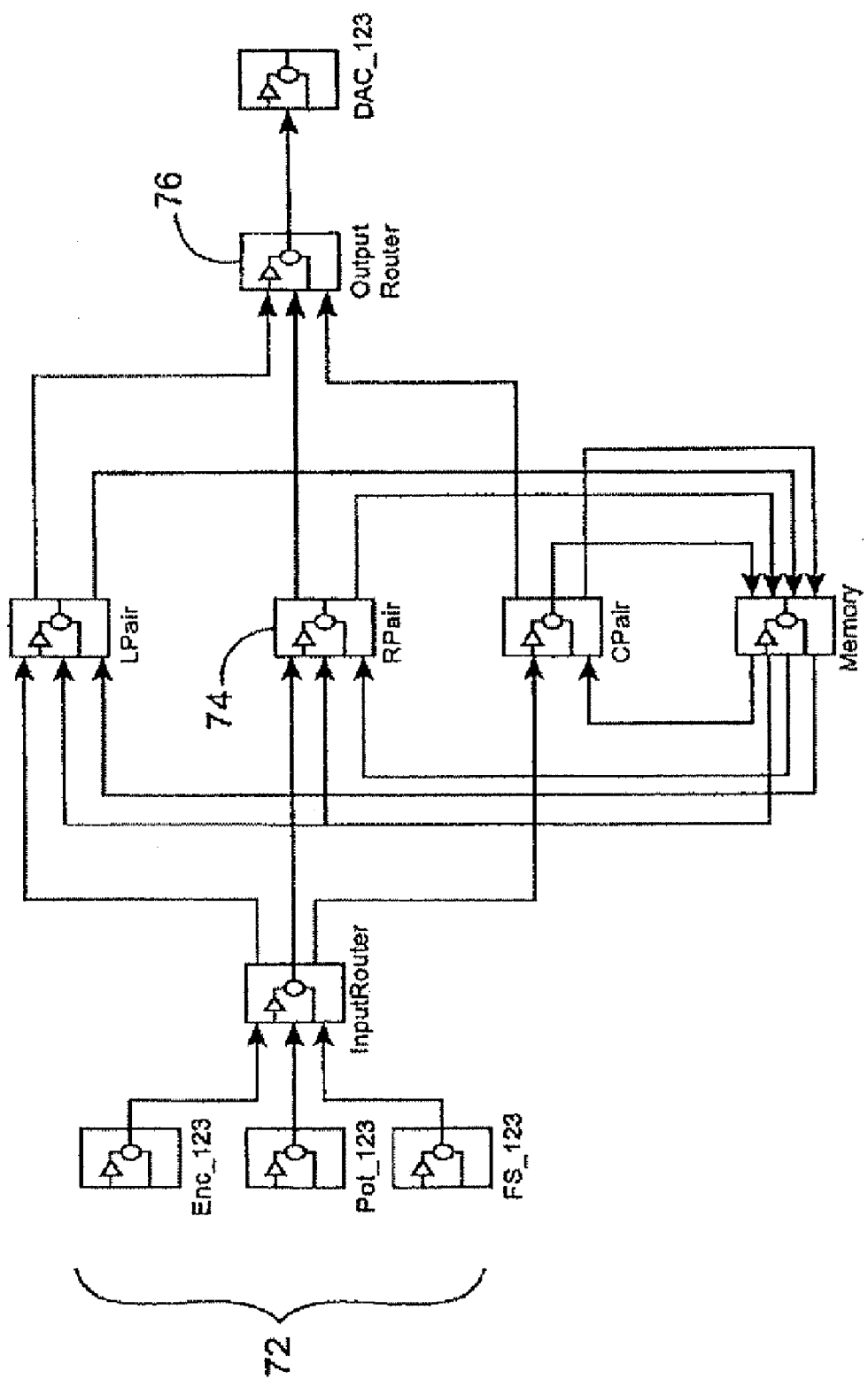
FIGS. 13A through C are graphic representations of computer code for implementing the control system of FIG. 12.

Referring now to FIG. 13A, a top level block diagram illustrates that input to the controller may arrive from a large number of individual encoders, potentiometers, and the like. These diagrams are printouts of the programming code using the Simulink™ programming language, commercially available from The Mathworks of Natick, Mass. As described above, both the master input device and robotic slave may have a significant number of joints, so that movement of an end effector in a single mode (such as grip or straight line translation) may actually change the configuration of several individual joints. The input information is routed, as appropriate, to a subroutine dedicated to a particular master/slave pair. For example, when changing the angle of gripping members held by the right hand of the operator, the robotic slave system illustrated in FIG. 4 will often vary the separation between end effector elements of a slave tool which is temporarily designated the right slave. Input for both the right master input controller device and right slave arm are directed to a right pair subroutine 74. Similar subroutines may be provided for the left pair, and for manipulation of the endoscopic camera by one or both master input devices. Output from, for example, the right pair control subroutine 74, is directed to an output router 76, which directs the torque signals to the appropriate motors of the slave system.

Figure 13B:
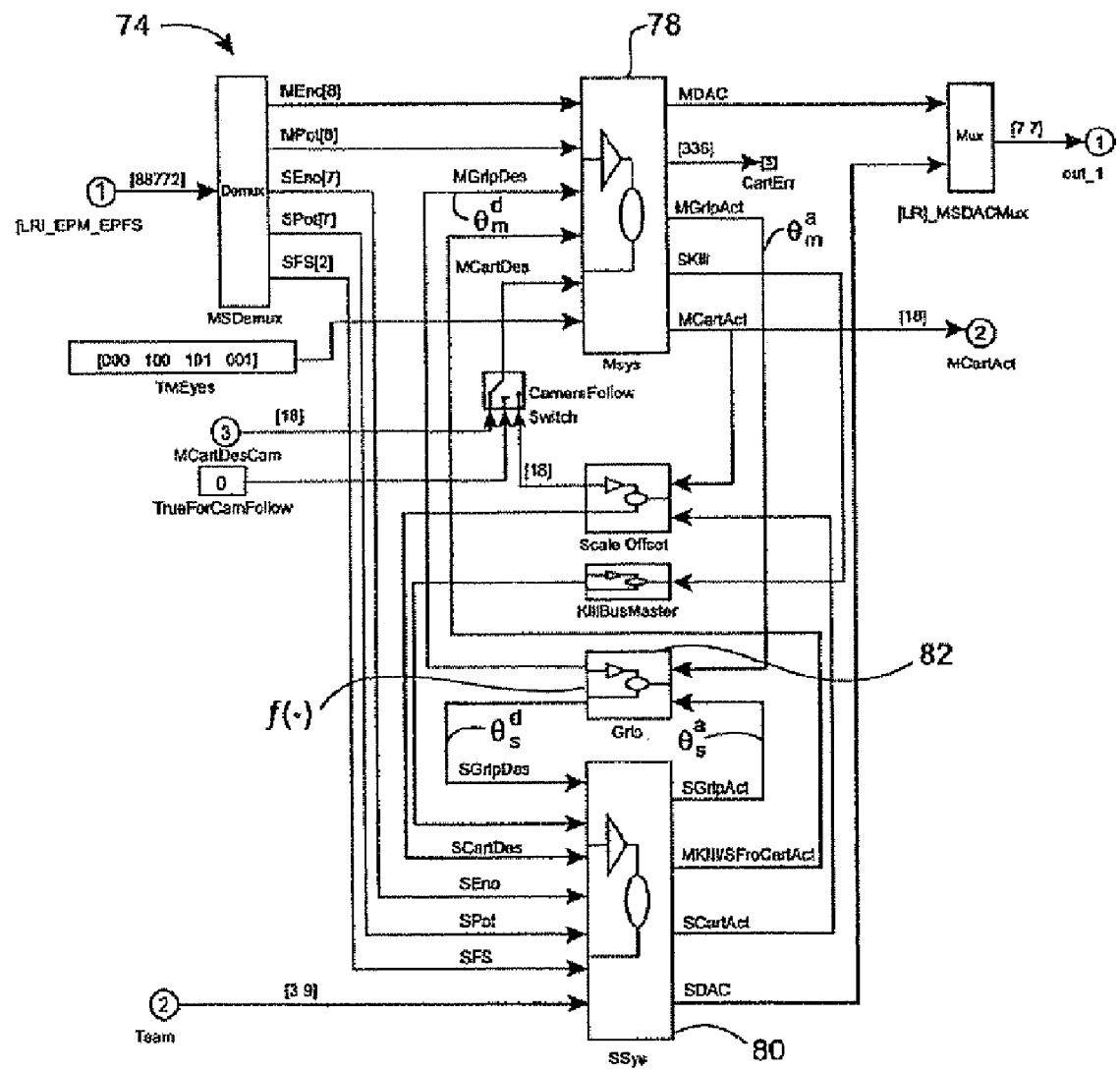

Referring now to FIG. 13B, the data processing performed within the right pair subroutine is illustrated in more detail. Position information from the encoders and potentiometers is demultiplexed and sent to a master controller subroutine 78 and/or slave controller subroutine 80. The actual master grip separation $\theta_m^a$ is operated upon by function F within a grip subroutine 82 so as to generate the desired slave separation $\theta_s^d$, as described above regarding FIGS. 9B and C. Optionally, the actual slave separation $\theta_s^a$ may be modified according to function g to determine the master desired separation $\theta_m^d$, as was described above regarding FIG. 9B.

Figure 13C:
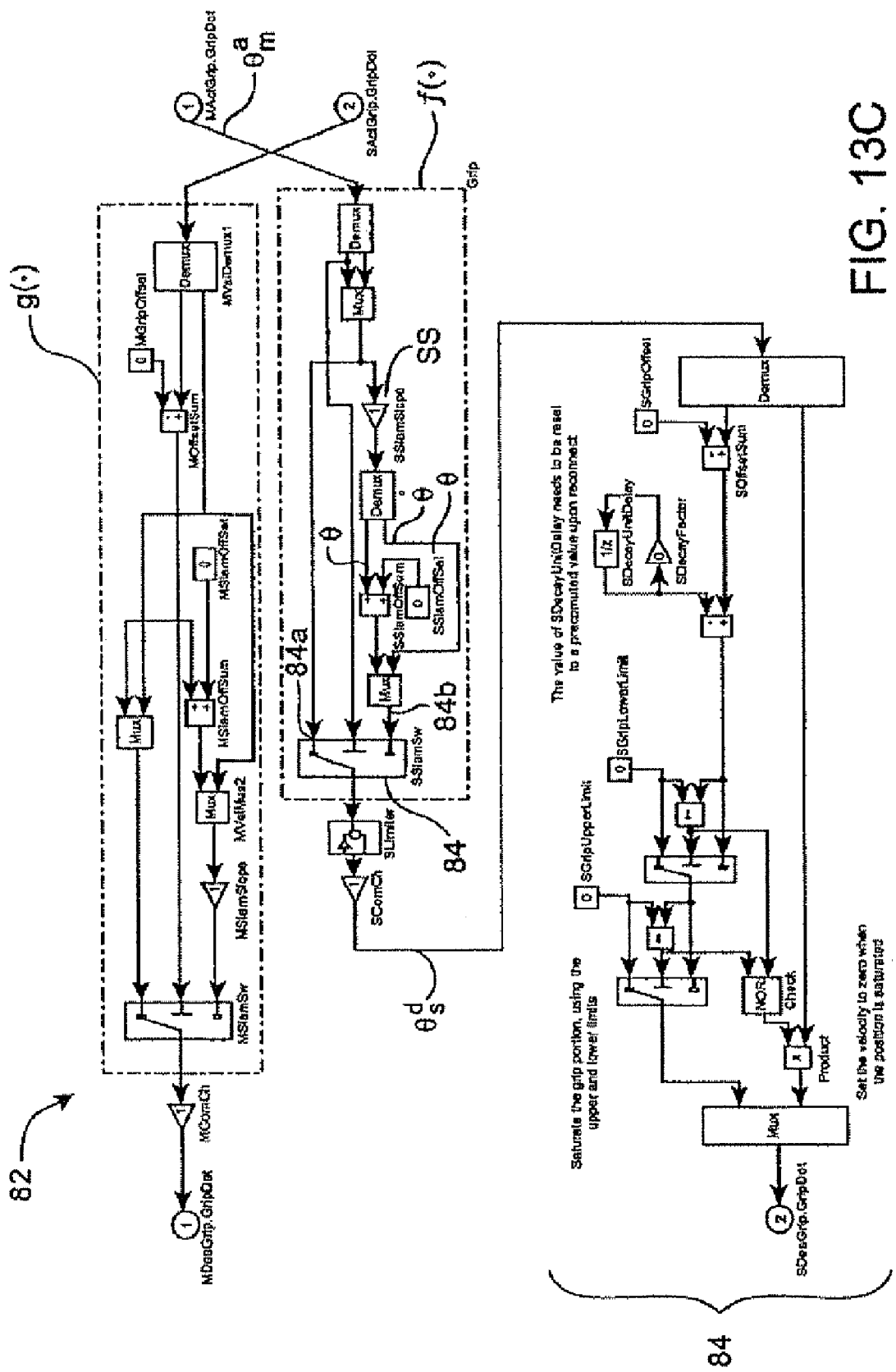

Referring now to FIG. 13C, a more detailed view of the operations performed by the grip subroutine 82 is illustrated. In the exemplary embodiment, handle 30 is unpowered so that function g is not implemented. To calculate the desired slave separation from the actual master separation, grip 82 determines whether the actual master separation is below predetermined point O (often arbitrarily set numerically equal to zero) at switch 84. If the master separation is greater than the predetermined amount, the master separation remains unchanged along path 84A. Otherwise, the master separation signal is modified according to path 84B, which changes the signal to enhance the error signal in following forces according to the slam slope SS. As described above, the slam slope is calculated based on the difference between maximum force point P and the predetermined point O (see FIG. 10). The slam offset is added so that the function $f$ is continuous at predetermined point O.

It should be noted that both position and velocity are modified by the bottom path. More specifically, when the position is modified, the velocity signal is also multiplied by the slam slope. Nonetheless, only position is used to determine which path to choose. Additionally, only position is adjusted to make the two paths match up continuously, as shown by the addition of offset to the position signal $\theta$, but not to the velocity signal $\dot{\theta}$.

In addition to implementing function $f$, the grip subroutine 82 also includes programming 84 to limit movement of the slave according to the particular mechanical configuration or use of a tool end effector, or according to the slave system capabilities and limits. This may be used, for example, to prevent inadvertent actuation of tools such as the clip applier illustrated in FIG. 8D from minor movement of the master grip elements.

While the preceding exemplary embodiments have been described in some detail, byway of example and for clarity of understanding, it should be noted that a variety of changes, modifications, and adaptations will be obvious to those of skill in the art. For example, although the embodiments of this invention have generally been described by focusing on predetermined master grip separation as a key to shifting from a position following type of control to force application control, the invention also has application by sensing the degree of separation of the slave end effectors, and switching control regimes upon the slave reaching a certain separation. The point of shifting control again could be determined by reaching a predetermined separation value. Alternatively, the end effector could be constructed with a sensing apparatus that senses when the end effectors contact an object to be gripped. At that point the control regime could shift from position control to force control, to better grip the object contacted. Moreover, much of the above description has assumed perfect transmission of forces based on motor torque signals, and the like. In truth, torques imposed by the motor will encounter significant "give" along the transmission system to end effector 56, so that additional spring-like resilience will be present in the system. Additionally, the enhanced grip forces described above may be applicable to a variety of master/slave robotic situations, particularly where the slave will be operating adjacent a movement constraint. Hence, the invention is limited solely by the appended claims.

What is claimed is:

1. In a medical robotic system, a handle coupled to first and second end effector elements through a processor so as to manipulate a separation between the first and second end effector elements through operator manipulation of the handle, the handle comprising:

first and second grip elements coupled together at conjoining ends of the first and second grip elements and defining a separation between free ends of the first and second grip elements; and at least one spring coupled to at least one of the first and second grip elements, wherein the at least one spring exhibits a first spring constant while the separation exceeds a separation transition point that corresponds to the free end of the first end effector element making contact with the free end of the second end effector element and exhibits a second spring constant greater than the first spring constant when the separation is less than the separation transition point.

2. The handle according to claim 1, wherein the at least one spring comprises:

first and second springs, wherein the first and second springs are configured so that the first spring is compressible throughout a full range of the separation and the second spring is compressible while the separation is less than the separation transition point.

3. The handle according to claim 2, wherein the first and second springs have different coil diameters so that one of the first and second springs is disposed within the coil of the other of the first and second springs.

4. The handle according to claim 3, wherein one end of the first spring is coupled to the first grip element and the other end of the first spring is coupled to the second grip element, and one end of the second spring is left free and the other end of the second spring is coupled to the second grip element so that the second spring is not compressed until after the first spring has been compressed to a point where the free end of the second spring makes contact with the first grip element.

5. The handle according to claim 1, wherein the at least one spring comprises:

a variable rate spring having first and second sections, wherein the first section has a first coil spacing and the second section has a second coil spacing that is larger than the first coil spacing.

6. The handle according to claim 5, wherein the first section is no longer compressible at the separation transition point and the second section is compressible at the separation transition point.

7. The handle according to claim 6, wherein the first section comprises a plurality of sections and the second section is coupled to and disposed between two of the plurality of sections.

8. The handle according to claim 1, wherein the second grip element has a stop and the at least one spring comprises:

a variable rate spring having first and second sections, wherein the first section has a first coil diameter smaller than a diameter of the stop and the second section has a second coil diameter that is larger than the diameter of the stop so that the first section compresses against the stop when the stop is disposed within the second section and the variable rate spring is compressed to at least the separation transition point.

* * * * *